(12) United States Patent
Onik

(10) Patent No.: US 11,696,797 B2
(45) Date of Patent: *Jul. 11, 2023

(54) CANCER IMMUNOTHERAPY BY RADIOFREQUENCY ELECTRICAL MEMBRANE BREAKDOWN (RF-EMB)

(71) Applicant: ImmunSYS, Inc., Fort Lauderdale, FL (US)

(72) Inventor: Gary Onik, Fort Lauderdale, FL (US)

(73) Assignee: ImmunSys, Inc., Fort Lauderdale, FL (US)

( * ) Notice: Subject to any disclaimer, the term of this patent is extended or adjusted under 35 U.S.C. 154(b) by 563 days.

This patent is subject to a terminal disclaimer.

(21) Appl. No.: 16/597,249

(22) Filed: Oct. 9, 2019

(65) Prior Publication Data
US 2020/0038093 A1 Feb. 6, 2020

Related U.S. Application Data

(63) Continuation of application No. 15/102,120, filed as application No. PCT/US2014/068774 on Dec. 5, (Continued)

(51) Int. Cl.
*A61B 18/12* (2006.01)
*A61B 18/14* (2006.01)
(Continued)

(52) U.S. Cl.
CPC .......... *A61B 18/14* (2013.01); *A61B 5/14532* (2013.01); *A61B 5/14539* (2013.01);
(Continued)

(58) Field of Classification Search
CPC ................ A61B 18/14; A61B 18/1477; A61B 2017/00061; A61B 2017/00159;
(Continued)

(56) References Cited

U.S. PATENT DOCUMENTS 4,483,338 A 11/1984 Bloom
5,139,496 A 8/1992 Hed et al.
(Continued)

FOREIGN PATENT DOCUMENTS

CN 1280513 A 1/2001
CN 1658924 A 8/2005
(Continued)

OTHER PUBLICATIONS

International Search Report and Written Opinion in PCT Appln. No. PCT/US2019/066876, dated Jun. 2, 2020, 11 pages.
(Continued)

*Primary Examiner* — Michael F Peffley
*Assistant Examiner* — Amanda L Zink
(74) *Attorney, Agent, or Firm* — Fish & Richardson P.C.

(57) ABSTRACT

A method of non-thermally ablating undesirable tissue in the body by application of pulsed, bipolar, instant charge reversal electrical fields of sufficient energy to cause complete and immediate cell membrane rupture and destruction. Energy is delivered through radio frequency pulses of particular frequencies, wave characteristics, pulse widths and pulse numbers, such that enhanced physical stresses are placed on the cell membrane to cause its immediate and complete destruction thereby spilling the entire cell content and membrane constituents into, the extracellular space without denaturing proteins so as to enable an immunological response to destroy and remove the target tissue and similarly marked tissue elsewhere in the subject.

30 Claims, 9 Drawing Sheets

Related U.S. Application Data 2014, now Pat. No. 10,849,678, which is a continuation of application No. 14/451,333, filed on Aug. 4, 2014, now Pat. No. 10,154,869.

(60) Provisional application No. 61/912,172, filed on Dec. 5, 2013.

(51) Int. Cl.
| | | |
|---|---|---|
| *A61N 1/32* | (2006.01) | |
| *A61B 5/145* | (2006.01) | |
| *A61B 5/00* | (2006.01) | |
| *A61M 5/00* | (2006.01) | |
| *A61B 18/00* | (2006.01) | |
| *A61B 17/00* | (2006.01) | |

(52) U.S. Cl.
CPC ........ *A61B 5/14546* (2013.01); *A61B 5/4839* (2013.01); *A61B 5/4848* (2013.01); *A61B 18/1477* (2013.01); *A61M 5/00* (2013.01); *A61N 1/325* (2013.01); *A61N 1/327* (2013.01); *A61B 2017/00061* (2013.01); *A61B 2017/00159* (2013.01); *A61B 2018/00577* (2013.01); *A61B 2018/00732* (2013.01); *A61B 2018/00821* (2013.01); *A61B 2018/00875* (2013.01); *A61B 2018/126* (2013.01); *A61M 2202/097* (2013.01); *A61M 2205/054* (2013.01)

(58) Field of Classification Search
CPC ........... A61B 2018/00577; A61B 2018/00732; A61B 2018/00821; A61B 2018/00875; A61B 2018/126; A61B 5/14532; A61B 5/14539; A61B 5/14546; A61B 5/4839; A61B 5/4848

See application file for complete search history.

(56) References Cited

U.S. PATENT DOCUMENTS

| | | | |
|---|---|---|---|
| 5,575,811 A | 11/1996 | Reid | |
| 5,672,174 A | 9/1997 | Gough et al. | |
| 5,931,807 A | 8/1999 | McClure | |
| 6,120,493 A * | 9/2000 | Hofmann | A61N 1/327 607/148 |
| 6,135,990 A * | 10/2000 | Heller | A61N 1/325 604/20 |
| 6,214,297 B1 | 4/2001 | Zhang et al. | |
| 6,241,702 B1 | 6/2001 | Lundquist | |
| 6,379,348 B1 | 4/2002 | Onik | |
| 6,408,199 B1 | 6/2002 | Goldin | |
| 6,482,619 B1 | 11/2002 | Rubinsky et al. | |
| 6,505,629 B1 | 1/2003 | Mikus et al. | |
| 6,575,969 B1 | 6/2003 | Rittman, III et al. | |
| 6,623,480 B1 | 9/2003 | Kuo et al. | |
| 6,733,485 B1 * | 5/2004 | Whitehurst | A61M 31/002 604/20 |
| 6,978,174 B2 | 12/2005 | Gelfand et al. | |
| 7,113,821 B1 | 9/2006 | Sun et al. | |
| 7,162,303 B2 | 1/2007 | Levin et al. | |
| 7,572,623 B2 | 8/2009 | Mangano et al. | |
| 7,620,451 B2 | 11/2009 | Demarais et al. | |
| 7,653,438 B2 | 1/2010 | Deem et al. | |
| 7,680,543 B2 | 3/2010 | Azure | |
| 7,744,878 B2 | 6/2010 | Mather | |
| 7,853,333 B2 | 12/2010 | Demarais | |
| 7,937,143 B2 | 5/2011 | Demarais et al. | |
| 7,938,824 B2 | 5/2011 | Chomenky | |
| 8,048,067 B2 | 11/2011 | Davalos et al. | |
| 8,114,070 B2 | 2/2012 | Rubinsky et al. | |
| 8,131,371 B2 | 3/2012 | Demarais et al. | |
| 8,145,316 B2 | 3/2012 | Deem et al. | |
| 8,221,411 B2 | 7/2012 | Francischelli et al. | |
| 8,226,648 B2 | 7/2012 | Paul et al. | |
| 8,231,603 B2 | 7/2012 | Hobbs et al. | |
| 8,282,631 B2 | 10/2012 | Davalos et al. | |
| 8,465,484 B2 | 6/2013 | Davalos et al. | |
| 8,814,860 B2 | 8/2014 | Davalos et al. | |
| 9,545,523 B2 | 1/2017 | Nanda | |
| 9,598,491 B2 | 3/2017 | Ahmed et al. | |
| 10,154,869 B2 | 12/2018 | Onik et al. | |
| 10,448,989 B2 | 10/2019 | Arena et al. | |
| 10,849,678 B2 | 12/2020 | Onik et al. | |
| 11,141,216 B2 | 10/2021 | Onik et al. | |
| 2001/0044596 A1 | 11/2001 | Jaafar | |
| 2002/0019644 A1 | 2/2002 | Hastings et al. | |
| 2002/0086014 A1 | 7/2002 | Korman et al. | |
| 2002/0087151 A1 | 7/2002 | Mody et al. | |
| 2002/0095124 A1 | 7/2002 | Palasis et al. | |
| 2002/0111617 A1 | 8/2002 | Cosman et al. | |
| 2002/0128640 A1 | 9/2002 | Swanson et al. | |
| 2002/0183684 A1 | 12/2002 | Dev et al. | |
| 2002/0193784 A1 | 12/2002 | McHale et al. | |
| 2002/0193789 A1 | 12/2002 | Underwood et al. | |
| 2002/0193833 A1 | 12/2002 | Dimmer et al. | |
| 2003/0018329 A1 | 1/2003 | Hooven | |
| 2003/0045495 A1 | 3/2003 | Li et al. | |
| 2003/0055471 A1 | 3/2003 | Fenn et al. | |
| 2003/0093067 A1 | 5/2003 | Panescu | |
| 2003/0153960 A1 | 8/2003 | Chornenky | |
| 2003/0163040 A1 | 8/2003 | Gildenberg | |
| 2003/0204161 A1 * | 10/2003 | Ferek-Petric | A61N 1/325 604/20 |
| 2003/0216722 A1 | 11/2003 | Swanson et al. | |
| 2003/0216792 A1 | 11/2003 | Levin et al. | |
| 2004/0143261 A1 | 7/2004 | Hartley et al. | |
| 2004/0248842 A1 | 12/2004 | Wagner et al. | |
| 2005/0182462 A1 | 8/2005 | Chomenky et al. | |
| 2005/0214268 A1 | 9/2005 | Cavanagh et al. | |
| 2005/0221270 A1 | 10/2005 | Connelly et al. | |
| 2005/0261672 A1 | 11/2005 | Deem | |
| 2005/0288667 A1 | 12/2005 | Thompson et al. | |
| 2005/0288730 A1 | 12/2005 | Deem et al. | |
| 2006/0041277 A1 | 2/2006 | Deem et al. | |
| 2006/0073589 A1 | 4/2006 | Belardelli et al. | |
| 2006/0149147 A1 | 7/2006 | Yanof | |
| 2006/0161246 A1 | 7/2006 | Rhim et al. | |
| 2006/0293725 A1 | 12/2006 | Rubinsky et al. | |
| 2006/0293730 A1 | 12/2006 | Rubinsky et al. | |
| 2007/0031338 A1 | 2/2007 | Zabinski | |
| 2007/0043345 A1 | 2/2007 | Davalos et al. | |
| 2007/0049919 A1 | 3/2007 | Lee | |
| 2007/0060989 A1 | 3/2007 | Deem | |
| 2007/0066957 A1 | 3/2007 | Demarais et al. | |
| 2007/0083193 A1 | 4/2007 | Werneth et al. | |
| 2007/0083239 A1 | 4/2007 | Demarais et al. | |
| 2007/0129720 A1 | 6/2007 | Demarais et al. | |
| 2007/0129760 A1 | 6/2007 | Demarais | |
| 2007/0233057 A1 | 10/2007 | Konishi | |
| 2008/0033417 A1 | 2/2008 | Nields et al. | |
| 2008/0058706 A1 | 3/2008 | Zhang et al. | |
| 2008/0071265 A1 | 3/2008 | Azure | |
| 2008/0132884 A1 | 6/2008 | Rubinsky et al. | |
| 2008/0132885 A1 | 6/2008 | Rubinsky et al. | |
| 2008/0208052 A1 | 8/2008 | LePivert et al. | |
| 2008/0247506 A1 | 10/2008 | Maschke | |
| 2008/0306476 A1 | 12/2008 | Hennings et al. | |
| 2008/0319375 A1 | 12/2008 | Hardy | |
| 2009/0028871 A1 | 1/2009 | Li et al. | |
| 2009/0088648 A1 | 4/2009 | Jaffe et al. | |
| 2009/0118727 A1 | 5/2009 | Pearson et al. | |
| 2009/0143717 A1 | 6/2009 | Bass | |
| 2009/0177094 A1 | 7/2009 | Brown et al. | |
| 2009/0292342 A1 | 11/2009 | Rubinsky et al. | |
| 2009/0326366 A1 | 12/2009 | Krieg | |
| 2010/0023004 A1 | 1/2010 | Francischelli et al. | |
| 2010/0030211 A1 | 2/2010 | Davalos et al. | |
| 2010/0049031 A1 | 2/2010 | Fruland et al. | |
| 2010/0049178 A1 | 2/2010 | Deem | |
| 2010/0069833 A1 | 3/2010 | Wenderow et al. | |
| 2010/0100092 A1 | 4/2010 | Turner et al. | |

(56) References Cited

U.S. PATENT DOCUMENTS

| | | |
|---|---|---|
| 2010/0152725 A1 | 6/2010 | Pearson et al. |
| 2010/0179530 A1 | 7/2010 | Long et al. |
| 2010/0221351 A1 | 9/2010 | He et al. |
| 2010/0249771 A1 | 9/2010 | Pearson et al. |
| 2010/0250209 A1 | 9/2010 | Pearson et al. |
| 2010/0261944 A1 | 10/2010 | Davalos et al. |
| 2010/0262067 A1 | 10/2010 | Chomenky et al. |
| 2010/0274178 A1 | 10/2010 | LePivert et al. |
| 2010/0331758 A1 | 12/2010 | Davalos et al. |
| 2011/0015630 A1 | 1/2011 | Azure |
| 2011/0082534 A1 | 4/2011 | Wallace |
| 2011/0106221 A1* | 5/2011 | Neal, II ............... A61B 18/12 607/2 |
| 2011/0112520 A1 | 5/2011 | Michael |
| 2011/0160514 A1 | 6/2011 | Long et al. |
| 2011/0160614 A1 | 6/2011 | Long et al. |
| 2011/0166499 A1 | 7/2011 | Demarais et al. |
| 2011/0190659 A1 | 8/2011 | Long et al. |
| 2011/0190764 A1 | 8/2011 | Long et al. |
| 2011/0202053 A1 | 8/2011 | Moss et al. |
| 2011/0217270 A1 | 9/2011 | Cavanagh, III et al. |
| 2012/0021481 A1 | 1/2012 | Hebner et al. |
| 2012/0041525 A1 | 2/2012 | Karni |
| 2012/0071749 A1 | 3/2012 | Xu et al. |
| 2012/0071872 A1 | 3/2012 | Rubinsky et al. |
| 2012/0071874 A1 | 3/2012 | Davalos et al. |
| 2012/0109122 A1 | 5/2012 | Arena et al. |
| 2012/0143181 A1 | 6/2012 | Demarais et al. |
| 2012/0190040 A1 | 7/2012 | Talebpour et al. |
| 2012/0215218 A1 | 8/2012 | Lipani |
| 2012/0215221 A1 | 8/2012 | Woloszko |
| 2012/0220998 A1 | 8/2012 | Long et al. |
| 2012/0220999 A1 | 8/2012 | Long |
| 2012/0221002 A1 | 8/2012 | Long et al. |
| 2012/0230939 A1 | 9/2012 | Perambakam et al. |
| 2012/0252087 A1 | 10/2012 | Hebner et al. |
| 2012/0253188 A1 | 10/2012 | Holland |
| 2012/0277741 A1 | 11/2012 | Davalos et al. |
| 2012/0277763 A1 | 11/2012 | Greenblatt |
| 2013/0108667 A1 | 3/2013 | Wang et al. |
| 2013/0101551 A1 | 4/2013 | Har-Noy |
| 2013/0071905 A1 | 5/2013 | Soikum et al. |
| 2013/0110098 A1 | 5/2013 | Lalonde |
| 2013/0184702 A1 | 7/2013 | Neal, II et al. |
| 2013/0189301 A1 | 7/2013 | Har-Noy |
| 2013/0211230 A1 | 8/2013 | Sperling |
| 2013/0237984 A1 | 9/2013 | Sklar |
| 2013/0289369 A1 | 10/2013 | Margolis |
| 2013/0295110 A1 | 11/2013 | Binder et al. |
| 2013/0302409 A1 | 11/2013 | Fuchs et al. |
| 2013/0304062 A1 | 11/2013 | Chan et al. |
| 2013/0310823 A1 | 11/2013 | Gefland et al. |
| 2013/0345697 A1 | 12/2013 | Garcia et al. |
| 2014/0012251 A1 | 1/2014 | Himmelstein et al. |
| 2014/0039491 A1 | 2/2014 | Basok et al. |
| 2014/0088578 A1 | 3/2014 | Rubinsky et al. |
| 2014/0172054 A1 | 6/2014 | Zarins et al. |
| 2014/0205609 A1 | 7/2014 | Valentine |
| 2014/0234296 A1 | 8/2014 | Sharma et al. |
| 2014/0257272 A1 | 9/2014 | Clark et al. |
| 2014/0328833 A1 | 11/2014 | Korman et al. |
| 2014/0350537 A1 | 11/2014 | Baust et al. |
| 2014/0356397 A1 | 12/2014 | Akle et al. |
| 2015/0150618 A1 | 6/2015 | Onik et al. |
| 2015/0190505 A1 | 7/2015 | Yeung |
| 2015/0201996 A1 | 7/2015 | Rubisky |
| 2015/0230850 A1 | 8/2015 | McKay |
| 2015/0265705 A1 | 9/2015 | Li et al. |
| 2015/0374436 A1 | 12/2015 | Subramaniam et al. |
| 2016/0128767 A1 | 5/2016 | Azamian et al. |
| 2016/0338754 A1 | 11/2016 | Baust et al. |
| 2016/0346354 A1 | 12/2016 | Heslet et al. |
| 2016/0367310 A1 | 12/2016 | Onik et al. |
| 2017/0020931 A1 | 1/2017 | Zhou et al. |
| 2017/0143780 A1 | 5/2017 | Zitvogel et al. |
| 2017/0274011 A1 | 9/2017 | Garibyan et al. |
| 2018/0021084 A1 | 1/2018 | Onik et al. |
| 2018/0028260 A1 | 2/2018 | Onik et al. |
| 2018/0028267 A1 | 2/2018 | Onik et al. |
| 2018/0133319 A1 | 5/2018 | Vo-Dinh et al. |
| 2018/0154142 A1 | 6/2018 | Guo et al. |
| 2018/0263685 A1 | 9/2018 | Onik et al. |
| 2018/0318365 A1 | 11/2018 | Yeung et al. |
| 2018/0318393 A1 | 11/2018 | Pierce et al. |
| 2019/0023804 A1 | 1/2019 | Onik et al. |
| 2019/0183561 A1 | 6/2019 | Hobbs et al. |
| 2019/0209652 A1 | 7/2019 | Pierce et al. |
| 2019/0241658 A1 | 8/2019 | Frederick |
| 2019/0298770 A1 | 10/2019 | Rabinovich et al. |
| 2020/0040095 A1 | 2/2020 | Onik et al. |
| 2020/0277379 A1 | 9/2020 | Bostwick et al. |
| 2021/0177491 A1 | 6/2021 | Onik et al. |

FOREIGN PATENT DOCUMENTS

| | | |
|---|---|---|
| CN | 101085391 A | 12/2007 |
| CN | 103118678 | 5/2013 |
| JP | 2001523987 | 11/2001 |
| JP | 2006187446 | 7/2006 |
| JP | 2009-297527 | 12/2009 |
| JP | 2010500153 | 1/2010 |
| JP | 2013/531043 | 8/2013 |
| JP | 5341287 | 11/2013 |
| JP | 2015-38492 A | 2/2015 |
| WO | WO 2004/037313 | 5/2004 |
| WO | WO 2008/034103 | 3/2008 |
| WO | WO 2010/080974 | 7/2010 |
| WO | WO 2012/088149 | 6/2012 |
| WO | WO 2012/99974 | 7/2012 |
| WO | WO 2013/053775 | 4/2013 |
| WO | WO 2013079980 | 6/2013 |
| WO | WO 2014/149690 | 9/2014 |
| WO | WO 2015/085162 | 6/2015 |
| WO | WO 2015/125159 | 8/2015 |
| WO | WO 2015/140150 | 9/2015 |
| WO | WO 2015/153639 | 10/2015 |
| WO | WO 2016/123608 | 8/2016 |
| WO | WO 2016/126778 | 8/2016 |
| WO | WO 2016/126811 | 8/2016 |
| WO | WO 2016/126905 | 8/2016 |
| WO | WO 2016/127162 | 8/2016 |
| WO | WO 2016123608 | 8/2016 |
| WO | WO 2016126778 | 8/2016 |
| WO | WO 2016126811 | 8/2016 |
| WO | WO 2016126905 | 8/2016 |
| WO | WO 2016127162 | 8/2016 |
| WO | WO 2017123981 | 7/2017 |

OTHER PUBLICATIONS

Royal, et al., "Phase 2 trial of single agent ipilimumab (anti-CLTA-4) for locally advanced or metastatic pancreatic adenocarcinoma," J. Immunother., 2010, 33(8):828-833.

Barnett et al., "Surgical ablation as treatment for the elimination of atrial fibrillation: a meta-analysis," The Journal of thoracic and cardiovascular surgery, May 1, 2006, 131(5):1029-35.

Cox et al,. "The surgical treatment of atrial fibrillation," The Journal of thoracic and cardiovascular surgery. 1991, 101(1-4):402-426, 569-592.

Cummings et al., "Alternative energy sources for the ablation of arrhythmias," Pacing and clinical electrophysiology, May 2005, 28(5):434-43.

Doll et al., "Esophageal perforation during left atrial radiofrequency ablation: is the risk too high?," The Journal of Thoracic and Cardiovascular Surgery, Apr. 1, 2003, 125(4):836-42.

Ninet et al., "Surgical ablation of atrial fibrillation with off-pump, epicardial, high-intensity focused ultrasound: results of a multi-center trial," The Journal of thoracic and cardiovascular surgery, Sep. 1, 2005, 130(3):803-e1.

PCT International Preliminary Report on Patentability in international Appln. No. PCT/US2016/016955, dated July 1, 2016, 6 pages.

(56) References Cited

OTHER PUBLICATIONS

PCT International Search Report and Written Opinion in international Appln. No. PCT/US2016/016955, dated July 1, 2016, 9 pages.
Viola et al., "The technology in use for the surgical ablation of atrial fibrillation," InSeminars in Thoracic and Cardiovascular Surgery, Jul. 1, 2002, 14(3):198-205.
Al Sakere et al., "A study of the immunological response to tumor ablation with irreversible electroporation," Technol Cancer Res Treat., Aug. 2007, 6(4):301-306.
Ammar et al., "Impact of a pulsed electric field on damage of plant tissues: effects of cell size and tissue electrical conductivity," J Food Sci., Jan.-Feb. 2011, 76(1):E90-7.
Arena et al. "High-Frequency Irreversible Electroporation (H-FIRE) for Non-Thermal Ablation without Muscle Contraction", Biomed Eng. Online Nov. 21, 2011, 10:102.
Aronsson et al., "Inactivation of *Escherichia coli*, Listeria innocua and *Saccharomyces cerevisiae* in relation to membrane permeabilization and subsequent leakage of intracellular compounds due to pulsed electric field processing," Int J Food Microbiol., Mar. 1, 2005, 99(1):19-32.
Asavasanti et al., "Critical electric field strengths of onion tissues treated by pulsed electric fields," J Food Sci., Sep. 2010, 75(7):E433-43.
Asavasanti et al., "Permeabilization of plant tissues by monopolar pulsed electric fields: effect of frequency," J Food Sci. Jan.-Feb. 2011, 76(1):E98-111.
Au et al., "Irreversible electroporation facilitates gene transfer of a GM-CSF plasmid with a local and systemic response," Surgery, Sep. 2013, 154(3):496-503.
Beebe et al., "Non-ionizing radiation with nanosecond pulsed electric fields as a cancer treatment: in vitro studies," Conf Proc IEEE Eng Med Biol Soc., Sep. 2-6, 2009, pp. 6509-6512.
Bertacchini et al., "Design of an irreversible electroporation system for clinical use," Technol Cancer Res Treat., Aug. 2007, 6(4):313-20.
Brooks et al., "Intratumoral injection of GM-CSF in perspective—A review," Journal of Medicine. Jan. 1, 2003, 34(1-6):149-53.
Chang et al. "Changes in Membrane Structure Induced by Electroporation as Revealed by Rapid-Freezing Electron Microscopy", Biophys J., Jul. 1, 1990, 58(1):1-12.
Chang et al., "Construction of a Genomic Map of H. pylori by Pulsed-Field Gel Electrophoresis (PFGE)," Methods Mol Med., 1997, 8:165-176.
Chen et al., "Leukemic cell intracellular responses to nanosecond electric fields," Biochem Biophys Res Commun., Apr. 30, 2004, 317(2):421-427.
Chen et al., "Membrane electroporation theories: a review," Med Biol Eng Comput., 2006, 44:5-14.
Chen et al., "Nanosecond electric pulses penetrate the nucleus and enhance speckle formation," Biochem Biophys Res Commun., Dec. 14, 2007, 364(2):220-225.
Chen et al., "Picosecond pulsed electric fields induce apoptosis in HeLa cells via the endoplasmic reticulum stress and caspase-dependent signaling pathways," Int J Oncol., Mar. 2013, 42(3):963-70.
Crowley "Electrical breakdown of bimolecular lipid membranes as an electromechanical instability," Biophys J., Jul. 1973, 13(7):711-724.
Djunzenova et al., "Effect of electric field pulses on the viability and on the membrane-bound immunoglobulins of LPS-activated murine B-lymphocytes: correlation with the cell cycle," Cymetry, Jan. 1, 1994, 15(1):35-45.
Dortch et al., "Characterization of pulsed magnetic field therapy in a rat model for rheumatoid arthritis," Biomed Sci Instrum., 2006, 42:302-307, Abstract Only.
Dyson et al., "Kinetic and physical studies of cell death induced by chemotherapeutic agents or hyperthermia," Cell Tissue Kinet., May 1986, 19(3):311-324.

EP Search Report in European Appln. No. 16744266.4, dated Oct. 18, 2018, 10 pages.
EP Search Report in European Appln. No. 17739066.3, dated Dec. 17, 2019, 20 pages.
Eppich et al., "Pulsed electric fields for selection of hematopoietic cells and depletion of tumor cell contaminants," Nat Biotechnol., Aug. 2000, 18(8):882-887.
Ersus et al., "Disintegration efficiency of pulsed electric field induced effects on onion (*Allium cepa* L.) tissues as a function of pulse protocol and determination of cell integrity by $^1$H-NMR relaxometiy," J Food Sci. Sep. 2010 ,75(7):E444-52.
Fehres et al,. "Understanding the biology of antigen cross-presentation for the design of vaccines against cancer," Frontiers in immunology. Apr. 8, 2014, 5:149.
Foltz, "Algae Lysis with Pulsed Electric Fields," California State Polytechnic University, San Luis Obispo 2012, [retrieved on May 13, 2019]retrieved from URL <http://digitalcommons.-calpoly.edu/theses/732/>, 76 pages.
García et al., "Biosynthetic requirements for the repair of sublethal membrane damage in *Escherichia coli* cells after pulsed electric fields," J Appl Microbiol., Mar. 2006, 100(3):428-435.
Garilevich et al., "Outlook for the use of focused shock waves and pulsed electric fields in the complex treatment of malignant neoplasms," Conf Proc IEEE Eng Med Biol Soc. 2006, 1:6370-6372.
Gómez-Ochoa et al., "Pulsed electromagnetic fields decrease proinflammatory cytokine secretion (IL-1$\beta$ and TNF-$\alpha$) on human fibroblast-like cell culture," Rheumatol Int., Oct. 2011, 31(10):1283-1289.
Gong et al., "Cancer Patient T Cells Genetically Targeted to Prostate-Specific Membrane Antigen Specifically Lyse Prostate Cancer Cells and Release Cytokines in Response to Prostate-Specific Membrane Antigen," Neoplasia, Jun. 1999, 1(2):123-127.
Gordon et al., "Intracellular hyperthermia. A biophysical approach to cancer treatment via intracellular temperature and biophysical alterations," Med Hypotheses., Jan. 1979, 5(1):83-102.
Grys et al., "Decreasing the thresholds for electroporation by sensitizing cells with local cationic anesthetics and substances that decrease the surface negative electric charge," Cell Mol Biol Lett., Mar. 2014, 19(1):65-76.
Hamid et al., "Safety and tumor responses with lambrolizumab (anti-PD-1) in melanoma," N Engl J Med., Jul. 11, 2013, 369(2):134-144.
Harris "Effects of Tumor-like assay conditions, Ionizing radiation, and hyperthermia on immune lysis of tumor cells by cytotoxic T-lymphocytes," Cancer Res., Aug. 1976, 36(8):2733-2739.
Hebb et al., "Systemic Antitumor Effects of Intratumoral Administration of the Novel Immunotherapeutic Combination Anti-CTLA4, Anti-CD137, and Anti-0X40 in Mouse Models of Lymphoma and Solid Tumor," Blood Journal, Dec. 3, 2015 126(23):1552.
Hillen et al., "Treatment of Metastatic Posterior Vertebral Body Osseous Tumors by Using a Targeted Bipolar Radiofrequency Ablation Device: Technical Note," Radiology, Jun. 13, 2014, 273(1):261-267.
Hua et al., "Intense picosecond pulsed electric fields induce apoptosis through a mitochondrial-mediated pathway in HeLa cells," Mol Med Rep., Apr. 2012, 5(4):981-987.
International Preliminary Report on Patentability in International Application No. PCT/US2014/068774, dated Jun. 7, 2016, 13 pages.
International Preliminary Report on Patentability in International Application No. PCT/US2016/015944, dated Aug. 1, 2017, 9 pages.
International Preliminary Report on Patentability in International Application No. PCT/US2016/016300, dated Aug. 8, 2017, 6 pages.
International Preliminary Report on Patentability in International Application No. PCT/US2016/016352, dated Aug. 8, 2017, 6 pages.
International Preliminary Report on Patentability in International Application No. PCT/US2016/016501, dated Aug. 8, 2017, 7 pages.
International Search Report and Written Opinion in International Application No. PCT/US2014/068774, dated Mar. 19, 2015, 15 pages.
International Search Report and Written Opinion in International Application No. PCT/US2016/015944, dated Jul. 29, 2016, 13 pages.

(56) References Cited

OTHER PUBLICATIONS

International Search Report and Written Opinion in International Application No. PCT/US2016/016300, dated Jul. 8, 2016, 9 pages.
International Search Report and Written Opinion in International Application No. PCT/US2016/016352, dated Jul. 18, 2016, 9 pages.
International Search Report and Written Opinion in International Application No. PCT/US2016/016501, dated Sep. 2, 2016, 10 pages.
Iu et al., "Reduction in levels of *Escherichia coli* O157:H7 in apple cider by pulsed electric fields," J Food Prot., Jul. 2001, 64(7):964-969.
Jaeger et al., "Protective effect of milk constituents and sublethal injuries limiting process effectiveness during PEF inactivation of Lb. rhamnosus," Int J Food Microbiol., Aug. 31, 2009, 134(1-2):154-161.
Jeffers et al., "Dimethylformamide as an enhancer of cavitation-induced cell lysis in vitro," J Acoust Soc Am., Jan. 1995, 97(1):669-676.
Jia et al., "Crystal stmeture of human grancalcin, a member of the penta-EF-hand protein family," J Mol Biol., Jul. 28, 2000, 300(5):1271-81.
JP Office action in Japanese Appln. No. 2017-540247, dated Nov. 26, 2019, 27 pages (with english translation).
Kawano et al., "Cryoimmunologic Antitumor Effects Enhanced by Dendritic Cells in Osteosarcoma", Clin Orthop Relat Res., May 2010, 468(5):1373-1383.
Kennedy et al., "Cationic Peptide Exposure Enhances Pulsed-Electric-Field-Mediated Membrane Disruption," PLoS One, Mar. 26, 2014, 9(3):e92528.
Kennedy et al., "Quantification of electroporative uptake kinetics and electric field heterogeneity effects in cells," Biophys J., Jun. 2008, 94(12):5018-5027.
Kim et al., "Changes of apoptosis in tumor tissues with time after irreversible electroporation," Biochem Biophys Res Commun., Jun. 14, 2013, 435(4):651-656.
Koga et al., "Interstitial Radiofrequency Hyperthermia for Brain Tumors," Neurol Med Chir., May 1993, 33(5):290-294.
Koster et al., "Recent developments and future challenges in immune checkpoint inhibitory cancer treatment," Current opinion in oncology, Nov. 1, 2015, 27(6):482-8.
Laufer et al., "Tissue Characterization Using Electrical Impedance Spectroscopy Data: A Linear Algebra Approach," Physiol Measu., 2012, 33:997-1013.
Lee et al., "Electron microscopic demonstration and evaluation of irreversible electroporation-induced nanopores on hepatocyte membranes," J Vasc Interv Radiol., Jan. 2012, 23(1):107-113.
Li et al., "Immunologic Response to Tumor Ablation with Irreversible Electroporation", PLOS One, Nov. 6, 2012, 7(11):e48749.
Li et al., "The effect of lipid molecular packing stress on cationic liposome-induced rabbit erythrocyte fusion," Biochim Biophys Acta., Jan. 14, 1997, 1323(1):105-116.
Lin et al., "Preparation of antioxidant peptide from egg white protein and improvement of its activities assisted by high-intensity pulsed electric field," J Sci Food Agric., May 2012, 92(7):1554-1561.
Ma et al., "Experimental Study on Residual Tumor Angiogenesis after Cryoablation," Asian Pac J Cancer Prev., 2014, 15(6):2491-2494.
Maor et al., "Irreversible electroporation attenuates neointimal formation after angioplasty," IEEE Trans Biomed Eng., Sep. 2008, 55(9):2268-2274.
Marx et al., "A comparative study on the structure of *Saccharomyces cerevisiae* under nonthermal technologies: high hydrostatic pressure, pulsed electric fields and thermo-sonication," Int J Food Microbiol., Dec. 15, 2011, 151(3)327-337.
Mi et al., "[Effect of steep pulsed electric fields on the immune response of tumor-bearing Wistar mice]," Sheng Wu Yi Xue Gong Cheng Xue Za Zhi., Apr. 2007, 24(2):253-256, Abstract Only.

Miller et al., "Integrated Carbon Fiber Electrodes within Hollow Polymer Microneedles for Transdermal Electrochemical Sensing," Biomicrofluidics., Mar. 30, 2011, 5(1):13415.
Miller et al., "Multiplexed microneedle-based biosensor array for characterization of metabolic acidosis," Talanta., Jan. 15, 2012, 88:739-742.
Milligan et al., "Interstitial Hyperthermia," Med Instrum., May-Jun. 1984, 18(3):175-180, Abstract Only.
Mishra et al., "Electric Property Sensing Biopsy Needle for Prostate Cancer Detection," Prostate, Nov. 2013, 73(15):1603-1613.
Morshed et al., "Electrical lysis: dynamics revisited and advances in On-chip operation,"Crit Rev Biomed Eng., 2013, 41(1):37-50.
Neal et al. "In Vitro and Numerical Support for Combinatorial Irreversible Electroporation and Electrochemotherapy Glioma Treatment", Annals of Biomedical Engineering, Mar. 2014, 42(3):475-487.
Neal et al., "Improved local and systemic anti-tumor efficacy for irreversible electroporation in immunocompetent versus immunodeficient mice," PLOS One., May 24, 2013, 8(5):e64559.
Neumann et al., "Permeability changes induced by electric impulses in vesicular membranes," J Membr Biol., Dec. 29, 1972, 10(3):279-290.
O'Dowd et al., "An assessment of the effect of pulsed electrical fields on tenderness and selected quality attributes of post rigour beef muscle," Meat Sci., Feb. 2013, 93(2):303-309.
Onik et al. "Irreversible Electroporation: Implications for Prostate Ablation", Technology in Cancer Res. and Treatment, Aug. 2007, 6(4): 295-300.
Onik et al. "Long-Term Results of Optimized Focal Therapy for Prostate Cancer: Average 10-Year Follow-Up in 70 Patients," Journal of Men's Health, Jun. 2014, 11(2):64-74.
Onik et al., "Three-Dimensional Sonographically Monitoring Cryosurgery in a Prostate Phantom," Journal of Ultrasound, 1996, 16:267-270.
Oshima et al., "Bacterial sterilization and intracellular protein release by a pulsed electric field," Adv Biochem Eng Biotechnol., Adv Biochem Eng Biotechnol., 2004, 90:113-33.
Peper et al., "An impedance-based cytotoxicity assay for real-time and label-free assessment of T-cell-mediated killing of adherent cells," J Immunol Methods, Mar. 2014, 405:192-198.
Persson et al., "A model for evaluating therapeutic response of combined cancer treatment modalities: applied to treatment of subcutaneously implanted brain tumors (N32 and N29) in Fischer rats with pulsed electric fields (PEF) and 60Co-gamma radiation (RT)," Technol Cancer Res Treat., Oct. 1, 2003, 2(5):459-470.
Poudineh et al., "Three-dimensional, sharp-tipped electrodes concentrate applied fields to enable direct electrical release of intact biomarkers from cells," Lab Chip., May 21, 2014, 14(10):1785-1790.
Ribas et al., "Dendritic cell vaccination combined with CTLA4 blockade in patients with metastatic melanoma," Clin Cancer Res., Oct. 1, 2019, 15(19):6267-6275.
Sabel et al. "Immunologic Response to Cryoablation of Breast Cancer," Breast Cancer Research and Treatment, Mar. 2005, 90(1):97-104.
Sabel et al., "Cryo-Immunology: A review of the literature and proposed mechanisms for stumulatory versus suppressive immune responses," Cryobiology, 2009, 58:1-11.
Sale et al., "Effects of high electric fields on micro-organisms. 3. Lysis of erythrocytes and protoplasts," Biochim Biophys Acta., Aug. 1968, 163(1):37-43.
Schaft et al., "A new way to generate cytolytic tumor-specific T cells: electroporation of RNA coding for a T cell receptor into T lymphocytes," Cancer Immunol Immunother., Sep. 2006,55(9):1132-1141.
Shen et al., "Abstract 4746: Modulation of suppressive myeloid populations by tasquinimod," Cancer Research, Apr. 15, 2013, 73:4746.
Shipman, "Microneedle Sensors May Allow Real-Time Monitoring of Body Chemistry," Dec. 13, 2011, [retrieved on May 15, 2019] retrieved from URL <https://news.ncsu.edu/2011/12/wmsnarayanmnsensors/>, 3 pages.

(56) References Cited

OTHER PUBLICATIONS

Somolinos et al., "Inactivation of *Escherichia coli* by citral," J Appl Microbiol., Jun. 2010,108(6):1928-1939.
Somolinos et al., "sigB absence decreased Listeria monocytogenes EGD-e heat resistance but not its Pulsed Electric Fields resistance," Int J Food Microbiol., Jun. 30, 2010, 141(1-2):32-38.
Stevenson et al., "Relationship between cell membrane potential and natural killer cell cytolysis in human hepatocellular carcinoma cells," Cancer Res., Sep. 1, 1989, 49(17):4842-4845.
Tang et al., "Steep pulsed electric fields modulate cell apoptosis through the change of intracellular calcium concentration," Colloids Surf B Biointerfaces., Jun. 15, 2007, 57(2):209-214.
Tarek, "Membrane Electroporation: a molecular dynamics Simulation," Biophys J., 2005, 88:4045-4053.
Traitcheva et al., "Electroporation and alternating current cause membrane permeation of photodynamic cytotoxins yielding necrosis and apoptosis of cancer cells," Bioelectrochemistry., Oct. 2010, 79(2):257-260.
U.S. Food and Drug Administration, "Kinetics of Microbial Inactivation for Alternative Food Processing Technologies—Pulsed Electric Fields", A Report of the Institute of Food Technologists for the Food and Drug Administration of the U.S. Department of Health and Human Services, Mar. 29, 2000, 108 pages.
Veiga et al., "Exposure of human leukemic cells to direct electric current: generation of toxic compounds inducing cell death by different mechanisms," Cell Biochem Biophys., 2005, 42(1):61-74.
Vora et al., "Interstitial implant with interstitial hyperthermia," Cancer, Dec. 1, 1982, 50(11):2518-2523.
Waitz et al. "Potent Induction of Tumor Immunity by Combining Tumor Cryoablation with Anti-CTLA-4 Therapy", Cancer Res., Jan. 2012, 72(2):430-439.
Williams et al., "Gene therapy approaches to prolonging corneal allograft survival," Expert Opin Biol Ther., Jul. 2004, 4(7):1059-1071.
Wouters et al., "Membrane permeabilization in relation to inactivation kinetics of *Lactobacillus* species due to pulsed electric fields," Appl Environ Microbiol., Jul. 2001, 67(7):3092-3101.
Yuan et al., "Immunologic responses to xenogeneic tyrosinase DNA vaccine administered by electroporation in patients with malignant melanoma," J Immunother Cancer, Nov. 18, 2013, 1:20.
Zheng et al., "Membrane microfilter device for selective capture, electrolysis and genomic analysis of human circulating tumor cells," J Chromatogr A., Aug. 31, 2007, 1162(2):154-61.
PRNewswire.com, "Image Guided Cancer Specialists Reports Successful Early Results from Cryoablation and Intra-tumoral Injection of Immunotherapy Drug Combination Yervoy and Keytruda for the Treatment of Cancer," Feb. 3, 2015, retrieved Nov. 17, 2020 from URL <https://www.prnewswire.com/news-releases/image-guided-cancer-specialists-reports-successful-early-results-from-cryoablation-and-intra-tumoral-injection-of-immunotherapy-drug-combination-yerivoy-and-keytruda-for-the-treatment-of-cancer-300029347.html>, 3 pages.
Williams, "The Immunotherapy Revolution: The Best New Hope for Saving Cancer Patients' Lives," Gatekeeper Press, Nov. 30, 2019, 115 pages.
AU Office Action in Australian Appln. No. 2020200688, dated Jun. 18, 2020, 5 pages.
U.S. Appl. No. 17/101,434, filed Nov. 23, 2020, Onik et al.
Aarts et al., "Cryoablation and immunotherapy: an overview of evidence on its synergy," Insights Into Imaging, Dec. 2019, 10(1), 12 pages.
Abdo et al. "Immunotherapy plus cryotherapy: potential augmented abscopal effect for advanced cancers," Frontiers in Oncology, Mar. 28, 2018, 8:85.
AMGen.com, "FDA Approves IMLYGIC™ (Talimogene Laherparepvec) as First Oncolytic Viral Therapy in the US," retrieved Aug. 13, 2020 from URL <https://www.amgen.com/media/news-releases/2015/10/fda-approves-imlygic-talimogene-laherparepvec-as-first-oncolytic-viral-therapy-in-the-us/, Oct. 27, 2015, 7 pages.
Arora et al., "Neoadjuvant Intratumoral Cytokine-Loaded Microspheres are Superior to Postoperative Autologous Cellular Vaccines in Generating Systematic Anti-Tumor Immunity," Journal of Surgical Oncology 94(5):403-412, dated Oct. 1, 2006.
Bastianpillai et al., "Harnessing the immunomodulatory effect of thermal and non-thermal ablative therapies for cancer treatment," Tumor Biology, Dec. 1, 2015, 36(12):9137-46.
Bulvik et al., "Irreversible electroporation versus radiofrequency ablation: a comparison of local and systemic effects in a small-animal model," Radiology, Aug. 2016, 280(2):413-24.
Chang et al., "Blocking of the PD-1/PD-L1 Interaction by ad-Peptide Antagonist for Cancer Immunotherapy," Angewandte Chemie International Edition, Sep. 28, 2015, 54(40):11760-4.
EP Extended Search Report in European Appln. No. 17739066.3, dated Dec. 16, 2019, 20 pages.
EP European Search Report in European Application No. 17739066, dated Aug. 13, 2019, 23 pages.
Fehres et al., "Understanding the Biology of Antigen Cross-Presentation for the Design of Vaccines Against Cancer," Frontiers in Immunology, Apr. 8, 2014, 5(149):1-10.
Immuno-OncologyNews.com, "Cryoablation Combined With Intratumoral Injection of Immunotherapeutic Drugs Offers Promising Outcomes," Feb. 10, 2015, 2 pages.
Ito et al., "Immune adjuvant activity of pre-resectional radiofrequency ablation protects against local and systemic recurrence in aggressive murine colorectal cancer," PLoS One, Nov. 23, 2015, 10(11):e0143370, 23 pages.
Jonathan et al., "Systemic Antitumor Effects of Intratumoral Administration of the Novel Immunotherapeutic Combination Anti-CTLA4, Anti-CD137, and Anti-OX40 in Mouse Models of Lymphoma and Solid Tumor," Blood, Jan. 1, 2015, 126(23):1552.
Koster et el., "Recent developments and future challenges in immune checkpoint inhibitory cancer treatment," Curr Opin Oncol., Nov. 2015, 27(6):482-488.
Machlenkin et al., "Combined dendritic cell cryotherapy of tumor induces systemic antimetastatic immunity," Clinical Cancer Research, Jul. 1, 2005, 11(13):4955-61.
Marabelle et al., "Intratumoral anti-CTLA-4 therapy: enhancing efficacy while avoiding toxicity," Clinical Cancer Research,Oct. 1, 2013, 19(19):5261, 4 pages.
Marabelle et al., "Intratumoral immunization: a new paradigm for cancer therapy," Clinical Cancer Research, Apr. 1, 2014, 20(7):1747-56.
Marabelle et al., "Intratumoral immunotherapy: using the tumor as teh remedy," Annals of Oncology, Dec. 1, 2017, 28:xii33-43, 11 pages.
Marabelle et al., "Starting the fight in the tumor: expert recommendations for the development of human intratumoral immunotherapy (HIT-IT)," Annals of Oncology, Nov. 1, 2018, 29(11):2163-74.
Mizukoshi et al., "Enhancement of tumor-associated antigen-specific T cell responses by radiofrequency ablation of hepatocellular carcinoma," Hepatology, Apr. 2013, 57(4):1448-57.
Paiella et al., "Local ablative strategies for ductal pancreatic cancer (radiofrequency ablation, irreversible electroporation): a review," Gastroenterology Research and Practice, Oct. 2016, vol. 2016, 10 pages.
PCT International Preliminary Report on Patentability in International Application No. PCT/US2017/013486, dated Jul. 17, 2018, 33 pages.
PCT International Search Report and Written Opinion in International Application No. PCT/US2017/013486, dated May 19, 2017, 38 pages.
Rosenberg et al., "Image guided cryoablation of cancer with intratumoral injection of anti-CTLA-4 and PD-1 immune check-point inhibitors," Journal for ImmunoTherapy of Cancer, Dec. 2015, 3(2):1-4.
Shi et al., "PD-1 blockade boosts radiofrequency ablation-elicited adaptive immune responses against tumor," Clinical Cancer Research, Mar. 1, 2016, 22(5):1173-84.
Sidana, "Cancer immunotherapy using tumor cryoablation," Immunotherapy, Jan. 2014, 6(1):85-93.

(56) References Cited

OTHER PUBLICATIONS

Somasundaram et al., "Nivolumab in Combination with Ipilimumab for the Treatment of Melanoma. Expert Review of Anti-Cancer Therapy," 15(10):1-13, dated Oct. 2015.
Waitz et al., "CTLA-4 blockade synergizes with cryoablation to mediate tumor rejection," Oncoimmunology, Jul. 1, 2012, 1(4):544-6.
Wang et al., "In Vitro Characterization of the Anti-PD-1 Antibody Nivolumab, BMS-936558, and In Vivo Toxicology in Non-Human Primates," Cancer Immunology Research 2(9):846-856, dated May 28, 2014.
Woolley et al., "Effect of Freezing Parameters (Freeze Cycle and Thaw Process) on Tissue Destruction Following Renal Cryoablation," Journal of Endourology 16(7):519-522, dated Sep. 2002.
Yu et al., "Treatment of osteosarcoma with microwave thermal ablation to induce immunogenic cell death," Oncotarget, Aug. 2014, 5(15):6526-39.
Zhou et al., "Structural repertoire of HIV-1-neutralizing antibodies targeting the CD4 supersite in 14 donors," Cell, Jun. 4, 2015, 161(6):1280-92.
CA Office Action in Canadian Appln. No. 2,932,765, dated Jul. 5, 2022, 7 pages.
CA Office Action in Canadian Appln. No. 2,975,123, dated Feb. 8, 2022, 4 pages.
Carosella et al., "A systematic review of immunotherapy in urologic cancer: evolving roles for targeting of CTLA-4, PD-1/PD-L1, and HLA-G," European Urology, Aug. 1, 2015, 68(2):267-79.
Chen et al., "Intratumoural GM-CSF microspheres and CTLA-4 blockade enhance the antitumour immunity induced by thermal ablation in a subcutaneous murine hepatoma model," International Journal of Hyperthermia, Jan. 1, 2009, 25(5):374-82.
CN Office Action in Chinese Appln. No. 201780012169.0, dated Mar. 14, 2022, 11 pages.
JP Japanese Office Action in Japanese Appln. No. 2018-555838, dated Jan. 24, 2022, 9 pages (with English translation).
JP Office action in Japanese Appln. No. 2016-536858, dated Nov. 12, 2019, 29 pages (with english translation).
Wikipedia.com [online], "Irreversible Electroporation," Sep. 8, 2018, retrieved on Sep. 11, 2019, retrieved from URL <https://en.wikipedia.org/wiki/Irreversible_electroporation>, 13 pages.

\* cited by examiner

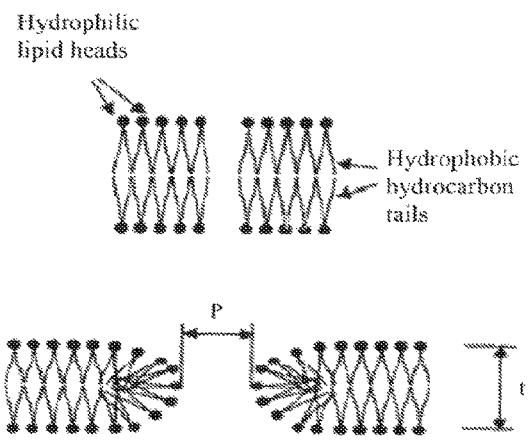
Fig. 1 - Prior Art
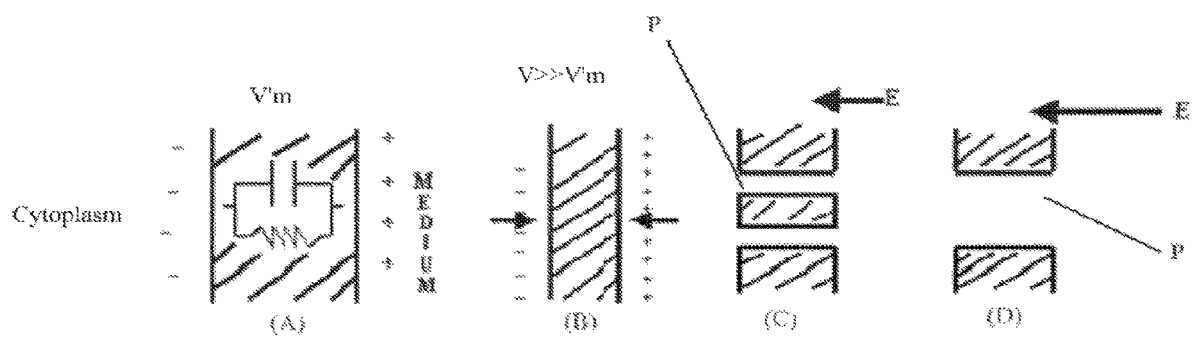
Fig. 2 - Prior Art

Probe distance = 1cm

| Protocol | Pulse Width | Pulse Number | Volts/ cm | Energy (mJ) | Total Time |
|---|---|---|---|---|---|
| 1* | 10 ms | 83 | 600 kV | 10.38 | .83 s |
| 2 | 200 us | 2490 | 10 kV | 10.38 | .49 s |
| 3 | 200 us | 2490+ | 10 kV or less | 10.38 | .49 s + |
| 4 | 200 us | 2490+ | 10 kV | 10.38 + | 4.9 s + |

Additional pulses added for decreased voltage caused by feedback

Additional pulses added for less efficient higher frequency

CANCER IMMUNOTHERAPY BY RADIOFREQUENCY ELECTRICAL MEMBRANE BREAKDOWN (RF-EMB)

CROSS REFERENCE TO RELATED APPLICATIONS

This patent application claims priority to U.S. Provisional Patent Application No. 61/912,172 filed Dec. 5, 2013 and titled "Cancer Antigen Enhanced Presentation to Antigen Presenting Cells by Radiofrequency Electrical Membrane Breakdown (RF-EMB) as an Adjuvant Mechanism for Immunotherapy," which is here incorporated in its entirety by reference. This patent application also claims priority to U.S. patent application Ser. No. 14/451,333, filed Aug. 4, 2014, now U.S. Pat. No. 10,154,869, and titled "System and Method For Creating Radio-Frequency Energy Electrical Membrane Breakdown For Tissue Ablation" which is here incorporated in its entirety by reference.

BACKGROUND OF THE INVENTION

1. Field of the Invention

The present invention relates generally to the field of medical ablation of biological tissue for treatment of disease and, more particularly, to the controlled application of radio frequency energy to soft tissue and cancerous tissue in humans and mammals to ablate such tissue through cellular destruction by Electrical Membrane Breakdown.

2. Description of the Background

Cancer is not one single disease but rather a group of diseases with common characteristics that often result in sustained cell proliferation, reduced or delayed cell mortality, cooption of bodily angiogenesis and metabolic processes and evasion of bodily immune response which results in undesirable soft tissue growths called neoplasms or, more commonly, tumors. Removal or destruction of this aberrant tissue is a goal of many cancer treatment methods and modalities. Surgical tumor excision is one method of accomplishing this goal. Tissue ablation is another, minimally invasive method of destroying undesirable tissue in the body, and has been generally divided into thermal and non-thermal ablation technologies. Thermal ablation encompasses both the addition and removal of heat to destroy undesirable cells. Cryoablation is a well established technique that kills cells by freezing of the extracellular compartment resulting in cell dehydration beginning at −15 C and by intracellular ice formation causing membrane rupture occurring at colder temperatures. Because cryoablative techniques can rupture the cell membrane without denaturing cell proteins under certain conditions, such techniques have the additional ability to stimulate an antitumor immune response in the patient.

Heat based techniques are also well established for ablation of both cancerous and non cancerous tissues and include radio-frequency (RF) thermal, microwave and high intensity focused ultrasound ablation which raise localized tissue temperatures well above the body's normal 37° C. These methods use various techniques to apply energy to the target cells to raise interstitial temperature. For example, RF thermal ablation uses a high frequency electric field to induce vibrations in the cell membrane that are converted to heat by friction. Cell death occurs in as little as 30 second once the cell temperature reaches 50° C. and decreases as the temperature rises. At 60° C. cell death is instantaneous. If the intracellular temperature rises to between about 60 and 95° C., the mechanisms involved in cell death include cellular desiccation and protein coagulation. When the intracellular temperature reaches 100° C., cellular vaporization occurs as intracellular water boils to steam. In the context of tissue ablation, cell temperatures not exceeding 50° C. are not considered clinically significant. Because cellular proteins are denatured by the heat of thermal ablation techniques, they are not available to stimulate a specific immune response as they may be with cryoablation. Both heat based and cryoablation techniques suffer from the drawback that they have little or no ability to spare normal structures in the treatment zone and so can be contraindicated based on tumor location or lead to complications from collateral injury.

Non thermal ablation techniques include electrochemotherapy and irreversible electroporation which although quite distinct from one another, each rely on the phenomenon of electroporation. With reference to FIG. 1, electroporation refers to the fact that the plasma membrane of a cell exposed to high voltage pulsed electric fields within certain parameters, becomes temporarily permeable due to destabilization of the lipid bilayer and the formation of pores P. The cell plasma membrane consists of a lipid bilayer with a thickness t of approximately 5 nm. With reference to FIG. 2A, the membrane acts as a nonconducting, dielectric barrier forming, in essence, a capacitor. Physiological conditions produce a natural electric potential difference due to charge separation across the membrane between the inside and outside of the cell even in the absence of an applied electric field. This resting transmembrane potential V'm ranges from 40 mv for adipose cells to 85 mv for skeletal muscle cells and 90 mv cardiac muscle cells and can vary by cell size and ion concentration among other things.

With continued reference to FIGS. 2B-2D, exposure of a cell to an externally applied electric field E induces an additional voltage V across the membrane as long as the external field is present. The induced transmembrane voltage is proportional to the strength of the external electric field and the radius of the cell. Formation of transmembrane pores P in the membrane occurs if the cumulative resting and applied transmembrane potential exceeds the threshold voltage which may typically be between 200 mV and 1 V. Poration of the membrane is reversible if the transmembrane potential does not exceed the critical value such that the pore area is small in relation to the total membrane surface. In such reversible electroporation, the cell membrane recovers after the applied field is removed and the cell remains viable. Above a critical transmembrane potential and with longer exposure times, poration becomes irreversible leading to eventual cell death due an influx of extracellular ions resulting in loss of homeostasis and subsequent apoptosis. Pathology after irreversible electroporation of a cell does not show structural or cellular changes until 24 hours after field exposure except in certain very limited tissue types. However, in all cases the mechanism of cellular destruction and death by IRE is apoptotic which requires considerable time to pass and is not visible pathologically in a time frame to be clinically useful in determining the efficacy of IRE treatment which is an important clinical drawback to the method.

Developed in the early 1990's, electrochemotherapy combines the physical effect of reversible cell membrane poration with administration of chemotherapy drugs such as cisplatin and bleomycin. By temporarily increasing the cell membrane permeability, uptake of non-permeant or poorly permeant chemotherapeutic drugs is greatly enhanced. After the electric field is discontinued, the pores close and the drug molecules are retained inside the target cells without significant damage to the exposed cells. This approach to chemotherapy grew out of earlier research developing electroporation as a technique for transfection of genes and DNA molecules for therapeutic effect. In this context, irreversible electroporation leading to cell death was viewed as a failure in as much as the treated cells did not survive to realize the modification as intended.

Irreversible electroporation (IRE) as an ablation method grew out of the realization that the "failure" to achieve reversible electroporation could be utilized to selectively kill undesired tissue. IRE effectively kills a predictable treatment area without the drawbacks of thermal ablation methods that destroy adjacent vascular and collagen structures. During a typical IRE treatment, one to three pairs of electrodes are placed in or around the tumor. Electrical pulses carefully chosen to induce an electrical field strength above the critical transmembrane potential are delivered in groups of 10, usually for nine cycles. Each 10-pulse cycle takes about one second, and the electrodes pause briefly before starting the next cycle. As described in U.S. Pat. No. 8,048,067 to Rubinsky, et. al and application Ser. No. 13/332,133 by Arena, et al. which are incorporated here by reference, the field strength and pulse characteristics are chosen to provide the necessary field strength for IRE but without inducing thermal effects as with RF thermal ablation. However, because cells ablated by IRE methods undergo apoptotic death without membrane rupture their ability to induce a supplemental immune response as observed with cryoablation is impaired. When used as the sole ablative tool in a treatment protocol, IRE's inability to induce a supplemental immune response is a substantial limitation to its therapeutic benefit for patients. On the other hand, cryoablation suffers from the significant clinical disadvantages arising from the extreme cold and its capacity to destroy nearby critical healthy structures. What is needed is a minimally invasive tissue ablation technology that can avoid damaging healthy tissue while exposing cellular contents without denaturing such cellular contents so that they can to trigger a clinically useful immune response.

SUMMARY OF TIE INVENTION

It is, therefore, an object of the present invention to provide a method of tissue ablation using electrical pulses which causes immediate cell death through the mechanism of complete break down the membrane of the cell.

It is another object of the present invention to provide a method of tissue ablation that causes immediate cell death electrically breaking down the cell membrane such that it can be monitored by immediate pathologic, chemical or spectroscopic examination of the tissue to evaluate efficacy of the treatment and adjust the same as needed.

It is yet another object of the present invention to provide a method of tissue ablation using electrical pulses that causes immediate cellular membrane breakdown non-thermally so that sensitive tissue structures are spared and the intra-cellular and membrane proteins are spilled into the extracellular space without denaturing to be exposed to the body's immune system in order to illicit a specific tumor immune response.

It is yet another object of the present invention to provide a method of tissue ablation that exposes non-denatured intra-cellular and membrane proteins to the immune system to illicit a specific tumor immune response which can be modulated and enhanced by a variety of additional immune modulators.

According to the present invention, the above described and other objects are accomplished, by applying to undesirable tissue in the body an external electric field specifically configured to directly and completely disintegrate the cell membrane. Referred to as Electrical Membrane Breakdown (EMB), application of an external oscillating electric field causes vibration and flexing of the cell membrane which results in a dramatic and immediate mechanical tearing or rupturing the cell membrane. EMB applies significantly higher energy levels than prior art methods to rupture the cell membrane rather than to electroporate the cell membrane. Unlike prior art methods, EMB expels the entire contents of the cell into the extracellular fluid and exposes internal components of the cell membrane which induces an inmmunologic response by the subject.

A system for generation of the electric field necessary to induce EMB includes a bipolar pulse generator operatively coupled to a controller for controlling generation and delivery of the electrical pulses necessary to generate an appropriate electric field. The field is generated by therapeutic probes placed in proximity to the soft tissue or cancerous cells within the body of the subject and the bipolar pulses are shaped, designed and applied to achieve that result in an optimal fashion. A temperature probe may be provided for temperature feedback to the controller which is configured to control the signal output characteristics of the signal generator. The EMB protocol calls for a series of short and intense bi-polar electric to generate an oscillating electric field between the electrodes that induce a similarly rapid and oscillating buildup of transmembrane potential across the cell membrane. The built up charge applies a an oscillating and flexing force to the cellular membrane which upon reaching a critical value causes extensive rupture of the membrane and spillage of the cellular content. In addition to being bi-polar, the electric pulses preferably trace a square wave form and are characterized by instant charge reversal that have substantially no relaxation time between the positive and negative polarities of the bi-polar pulse. Instant charge reversal pulses are significantly more effective in destruction of dielectric cell membranes Important characteristic of the applied electric field include the field strength (Volts/cm), frequency, polarity, shape, duration, number and spacing. Field strength (Volts/cm) is a function of both the applied voltage and the electrode spacing and is preferably in the range of 1.500 V/cm to 10,000 V/cm absent thermal considerations. RF-EMB ablation is preferably performed by application of a series of not less than 100 electric pulses in a pulse train so as to impart the energy necessary on the target tissue without developing thermal issues in any clinically significant way. The pulse duration is preferably from 100 to 1000 μs. The relationship between the duration and frequency of each pulse determines the number of instantaneous charge reversals experienced by the cell membrane during each pulse. The duration of each inter pulse burst interval is determined by the controller 14 based on thermal considerations. Real time temperature feedback of the treatment site may be provided to the controller by which the controller can modulate treatment parameters to eliminate thermal effects as desired. Current flow at the treatment site may also be monitored for this purpose.

The EMB ablation method is carried out by first identifying the location of the soft tissue within the subject to be ablated by medical imaging techniques such as CT or MRI or other means. A preferred position and spacing of the electrodes relative to the target tissue is determined and from 1 to 6 needle electrodes connected to the controller and signal generator are inserted into position in and around the treatment site. Placement and positioning of the electrodes is confirmed by medical imaging and the pulse generator is activated to apply electrical pulses to the electrodes to generate the treatment field thereby causing electrical membrane breakdown of cells in the soft tissue.

Electrical membrane breakdown causes immediate spillage of all intracellular components of the ruptured cells into an extracellular space and exposes the internal constituent parts of the cell and cell membrane including antigens which induce an immunologic response to destroy and remove this and like material in the body of the subject. The immunologic response can be enhanced by administration of agents that increase the immunologic response process including drugs. Electrical membrane breakdown causes immediate, visually observable tissue change, cellular membrane destruction and cell death such that the method may include the biopsy of a portion of the treated target tissue to verify treatment efficacy immediately after completion of the treatment while the patient is still in position for additional treatment. In other embodiments needle probes placed in critical treatment locations could monitor various parameters by means of chemical or spectroscopic means related to the immediate destruction and spillage of the intracellular contents also to verify treatment efficacy. In some situation, the mode of treatment may be switched from EMB to thermal ablation without removal or repositioning of the electrodes by reconfiguring the signal generated by the pulse generator to increase the tissue temperature at the electrodes according to known RF thermal techniques.

BRIEF DESCRIPTION OF THE DRAWINGS

FIG. 1 is a diagram of a cell membrane pore.

FIG. 2 is a diagram of cell membrane pore formation by a prior art method.

DETAILED DESCRIPTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not limit the scope of the invention.

Irreversible electroporation as a tissue ablation method is well developed with commercially manufactured equipment such as the NanoKnife by AngioDynamics (Latham, N.Y.) available on the market. As described, this ablation technique utilizes high electric field strengths, within specific parameters, to induce irreversible electroporation of the cell membrane resulting in eventual cell death due to loss of homeostasis and apoptosis. The present invention also describes methods for ablating cells within the body of a subject utilizing high frequency and high strength electric fields but does so through the entirely different process of Electrical Membrane Breakdown (EMB) using very different energy characteristics. Electrical Membrane Breakdown is the application of an external oscillating electric field to cause vibration and flexing of the cell membrane which results in a dramatic and immediate mechanical tearing, disintegration or rupturing of the cell membrane. Unlike IRE, in which nano-pores are created in the cell membrane but through which little or no content of the cell is released, EMB completely tears open the cell membrane such that the entire contents of the cell are expelled into the extracellular fluid, and internal components of the cell membrane itself are exposed.

The present invention relies on the interaction of an applied electric field with the transmembrane potential but its similarity to IRE ends there. EMB applies significantly higher energy levels by specifically configured electric field profiles to directly and completely disintegrate the cell membrane rather than to electroporate the cell membrane. Others have demonstrated that the energy levels required for EMB is 100 times greater than for IRE using the same pulse configurations (pulse number and voltage density) delivered by currently available IRE equipment and protocols. The inability of current IRE methods and energy protocols to deliver the energy necessary to cause EMB explains why pathologic examination of IRE treated specimens has never shown the pathologic characteristics of EMB and is a critical reason why EMB had not until now been recognized as an alternative method of cell destruction.

Figure 9:
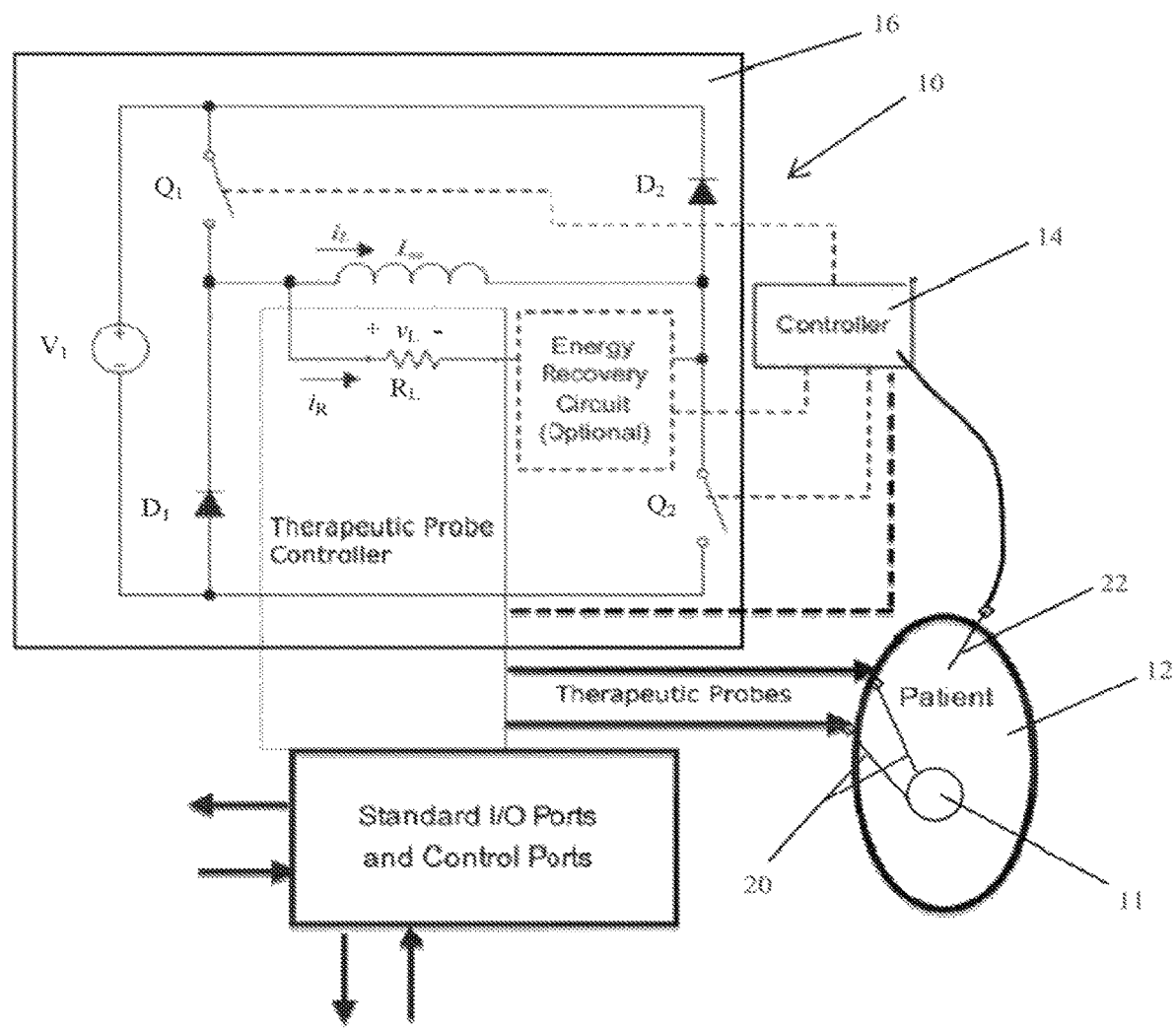
FIG. 9 is a schematic diagram of a pulse generation and delivery system for application of the method of the present invention.

FIG. 9 is a schematic diagram of a system 10 for generation of the electric field necessary to induce EMB of cells 11 within a patient 12. The system 10 includes a bipolar pulse generator 16 operatively coupled to a controller 14 for controlling generation and delivery to the therapeutic probe or probes 20 (two are shown) of the electrical pulses necessary to generate an appropriate electric field to achieve EMB. The therapeutic probes are placed in proximity to the soft tissue or cancerous cells 11 which are intended to be ablated through the process of EMB and the bipolar pulses are shaped, designed and applied to achieve that result in an optimal fashion. A temperature probe 22 may be provided for percutaneous temperature measurement and feedback to the controller of the temperature at or near the electrodes. The controller may preferably include an onboard digital processor and a memory and may be a general purpose computer system, programmable logic controller or similar digital logic control device. The controller is preferably configured to control the signal output characteristics of the signal generation including the voltage, frequency, shape, polarity and duration of pulses as well as the total number of pulses delivered in a pulse train and the duration of the inter pulse burst interval.

With reference to FIG. 9, the EMB protocol calls for a series of short and intense bi-polar electric pulses delivered from the pulse generator through one or more therapeutic probes 20 (electrodes) inserted directly into, or placed around the target tissue 1. The bi-polar pulses generate an oscillating electric field between the electrodes that induce a similarly rapid and oscillating buildup of transmembrane potential across the cell membrane. The built up charge applies an oscillating and flexing, force to the cellular membrane which upon reaching a critical value causes rupture of the membrane and spillage of the cellular content. Bipolar pulses are more lethal than monopolar pulses because the pulsed electric field causes movement of charged molecules in the cell membrane and reversal in the orientation or polarity of the electric field causes a corresponding change in the direction of movement of the charged molecules and of the forces acting on the cell. The added stresses that are placed on the cell membrane by alternating changes in the movement of charged molecules create additional internal and external changes that cause indentations, crevasses, rifts and irregular sudden tears in the cell membrane causing more extensive, diverse and random damage and disintegration of the cell membrane.

Figure 3:
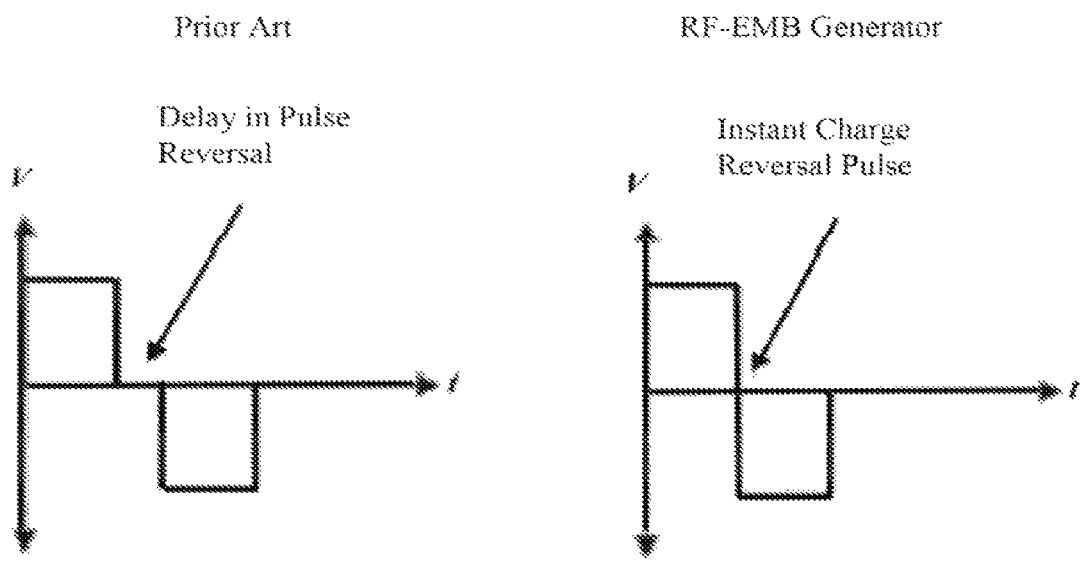
FIG. 3 is a comparison of a prior art charge reversal with an instant charge reversal according to the present invention.
Figure 4:
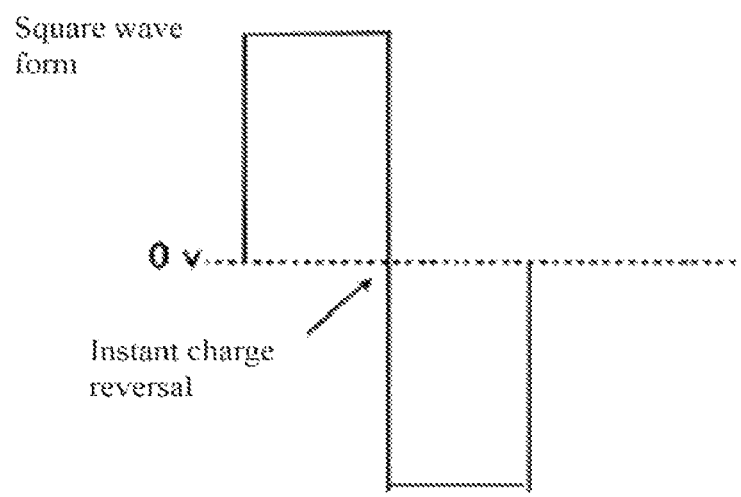
FIG. 4 is a square wave from instant charge reversal pulse according to the present invention.

With reference to FIG. 4, in addition to being bi-polar, the preferred embodiment of electric pulses is one for which the voltage over time traces a square wave form and is characterized by instant charge reversal pulses (ICR). A square voltage wave form is one that maintains a substantially constant voltage of not less than 80% of peak voltage for the duration of the single polarity portion of the trace, except during the polarity transition. An instant charge reversal pulse is a pulse that is specifically designed to ensure that substantially no relaxation time is permitted between the positive and negative polarities of the bi-polar pulse. That is, the polarity transition happens virtually instantaneously.

The destruction of dielectric cell membranes through the process of Electrical Membrane Breakdown is significantly more effective if the applied voltage pulse can transition from a positive to a negative polarity without delay in between. Instant charge reversal prevents rearrangement of induced surface charges resulting in a short state of tension and transient mechanical forces in the cells, the effects of which are amplified by large and abrupt force reversals. Alternating stress on the target cell that causes structural fatigue is thought to reduce the critical electric field strength required for EMB. The added structural fatigue inside and along the cell membrane results in or contributes to physical changes in the structure of the cell. These physical changes and defects appear in response to the force applied with the oscillating EMB protocol and approach dielectric membrane breakdown as the membrane position shifts in response to the oscillation, up to the point of total membrane rupture and catastrophic discharge. This can be analogized to fatigue or weakening of a material caused by progressive and localized structural damage that occurs when a material is subjected to cyclic loading, such as for example a metal paper clip that is subjected to repeated bending. The nominal maximum stress values that cause such damage may be much less than the strength of the material under ordinary conditions. The effectiveness of this waveform compared to other pulse waveforms can save up to ⅕ or ⅙ of the total energy requirement.

Figure 10:
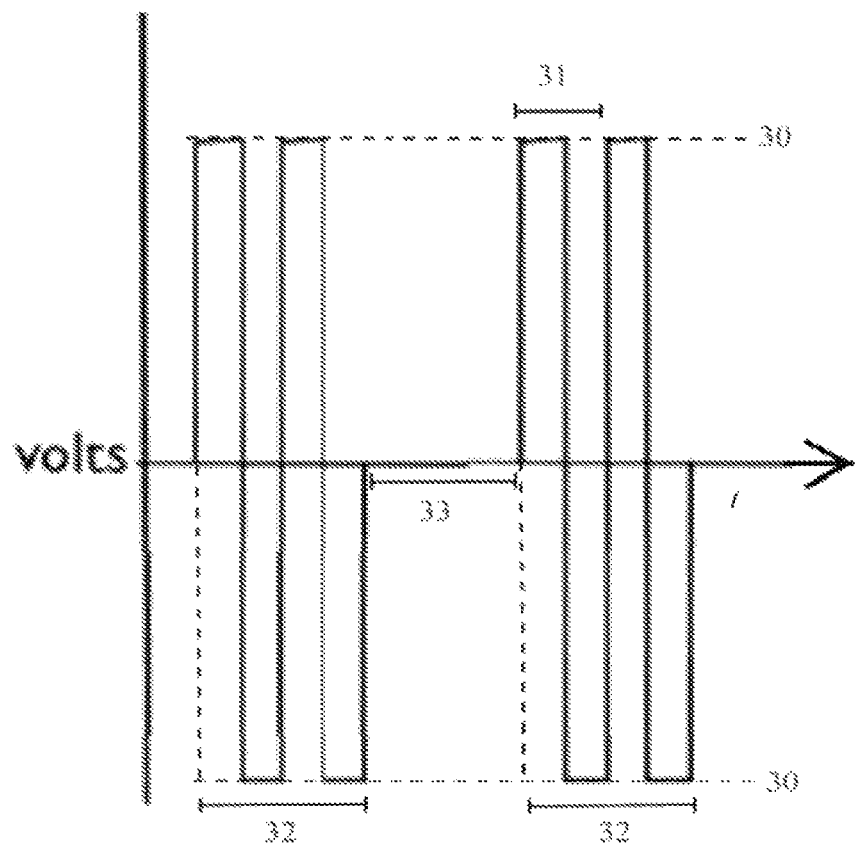
FIG. 10 is a diagram of the parameters of a partial pulse train according to the present invention.

With reference to FIG. 10, another important characteristic of the applied electric field is the field strength (Volts/cm) which is a function of both the voltage 30 applied to the electrodes by the pulse generator 16 and the electrode spacing. Typical electrode spacing for a bi-polar, needle type probe might be 1 cm, while spacing between multiple needle probe electrodes can be selected by the surgeon and might typically be from 0.75 cm to 1.5 cm. A pulse generator for application of the present invention is capable of delivering up to a 10 kV potential. The actual applied field strength will vary over the course of a treatment to control circuit amperage which is the controlling factor in heat generation, and patient safety (preventing large unanticipated current flows as the tissue impedance falls during a treatment). Where voltage and thus field strength is limited by heating concerns the duration of the treatment cycle may be extended to compensate for the diminished charge accumulation. Absent thermal considerations, a preferred field strength for EMB is in the range of 1,500 V/cm to 10,000 V/cm.

Figure 5:
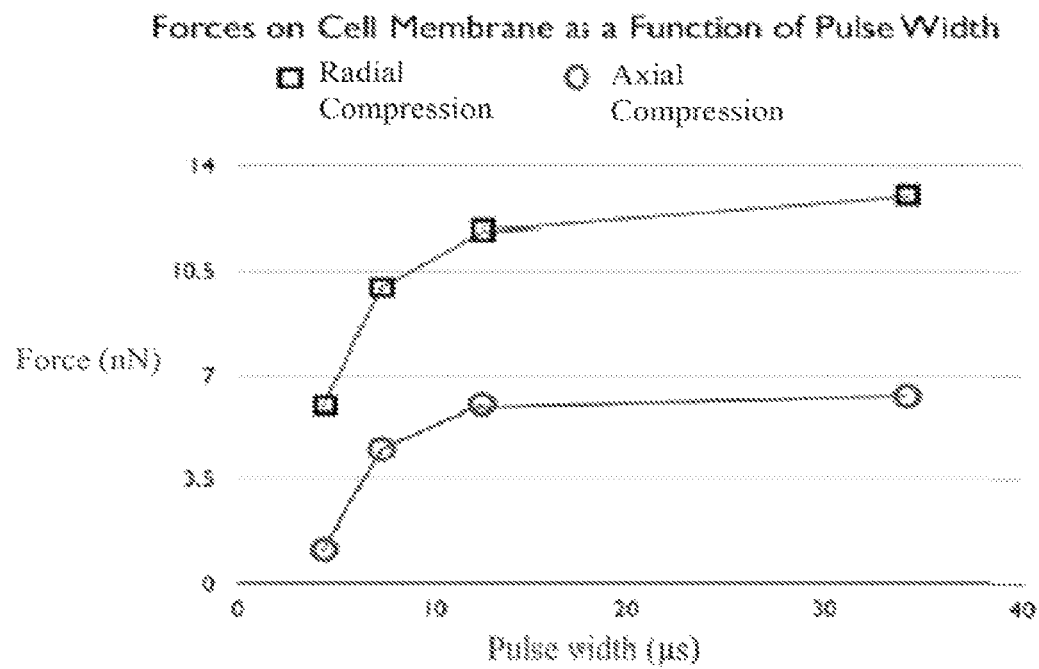
FIG. 5 is a diagram of the forces imposed on a cell membrane as a function of electric field pulse width according to the present invention.

With continued reference to FIG. 10, the frequency 31 of the electric signal supplied to the electrodes 20, and thus of the field polarity oscillations of the resulting electric field, influences the total energy imparted on the subject tissue and thus the efficacy of the treatment but are less critical than other characteristics. A preferred signal frequency is from 14.2 kHz to less than 500 kHz. The lower frequency bound imparts the maximum energy per cycle below which no further incremental energy deposition is achieved. With reference to FIG. 5 the upper frequency limit is set based on the observation that above 500 kHz, the polarity oscillations are too short to develop enough motive force on the cell membrane to induce the desired cell membrane distortion and movement. More specifically, at 500 kHz the duration of a single full cycle is 2 μs of which half is of positive polarity and half negative. When the duration of a single polarity approaches 1 μs there is insufficient time for charge to accumulate and motive force to develop on the membrane. Consequently, membrane movement is reduced or eliminated and EMB does not occur. In a more preferred embodiment the signal frequency is from 100 kHz to 450 kHz. Here the lower bound is determined by a desire to avoid the need for anesthesia or neuromuscular-blocking drugs to limit or avoid the muscle contraction stimulating effects of electrical signals applied to the body. The upper bound in this more preferred embodiment is suggested by the frequency of radiofrequency thermal ablation equipment already approved by the FDA, which has been deemed safe for therapeutic use in medical patients In addition to controlling the pulse amplitude 30, frequency 31, polarity and shape provided by the pulse generator 16, the logic controller 14 controls the number of pulses 32 to be applied in the treatment series or pulse train, the duration of each pulse 32, and the inter pulse burst delay 33. Although only two are depicted in FIG. 10 due to space constraints, RF-EMB ablation is preferably performed by application of a series of not less than 100 electric pulses 32 in a pulse train so as to impart the energy necessary on the target tissue 11 without developing thermal issues in any clinically significant way. The width of each individual pulse 32 is preferably from 100 to 1000 μs with an inter pulse burst interval 33 during which no voltage is applied in order to facilitate heat dissipation and avoid thermal effects. The relationship between the duration of each pulse 32 and the frequency 31 (period) determines the number of instantaneous charge reversals experienced by the cell membrane during each pulse 32. The duration of each inter pulse burst interval 33 is determined by the controller 14 based on thermal considerations. In an alternate embodiment the system 10 is further provided with a temperature probe 22 inserted proximal to the target tissue 11 to provide a localized temperature reading at the treatment site to the controller 14. The temperature probe 22 may be a separate, needle type probe having a thermocouple tip, or may be integrally formed with or deployed from one or more of the needle electrodes. With temperature feedback in real time, the controller can modulate treatment parameters to eliminate thermal effects as desired by comparing the observed temperature with various temperature set points stored in memory. More specifically, the controller can shorten or increase the duration of each pulse 32 to maintain a set temperature at the treatment site to, for example, create a heating (high temp) for the needle tract to prevent bleeding or to limit heating (low temp) to prevent any coagulative necrosis. The duration of the inter pulse burst interval can be modulated in the same manner in order to eliminate the need to stop treatment and maximizing the deposition of energy to accomplish RF-EMB. Pulse amplitude 30 and total number of pulses in the pulse train may also be modulated for the same purpose and result.

Figure 6:
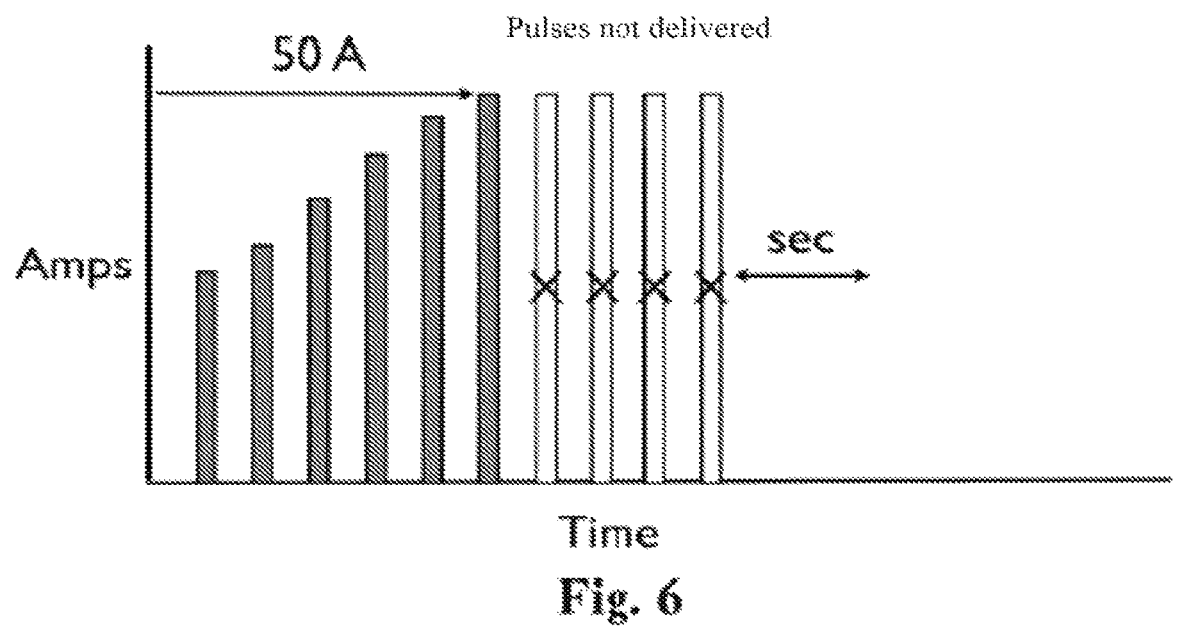
FIG. 6 is a diagram of a prior art failure to deliver prescribed pulses due to excess current.
Figure 7:
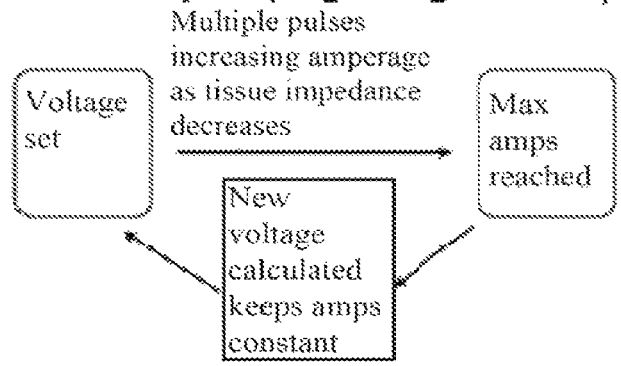
FIG. 7 is a schematic diagram of a feedback loop according to the present invention by which a controller reduces an applied signal voltage to keep the current amperage at or below a maximum.
Figure 8:
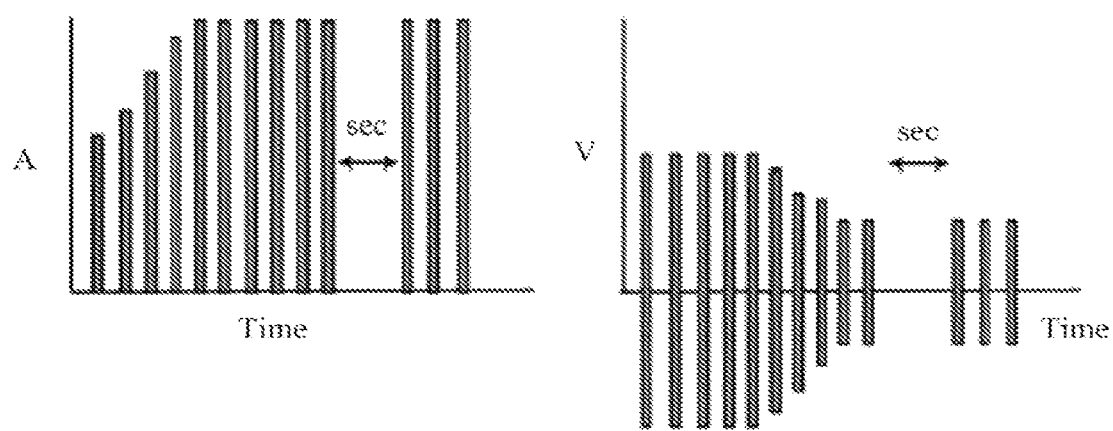
FIG. 8 is a diagram of a reduction in applied signal voltage upon reaching a maximum current level to permit continued signal delivery according to the present invention.

In yet another embodiment, the controller may monitor or determine current flow through the tissue during treatment fir the purpose of avoiding overheating while yet permitting treatment to continue by reducing the applied voltage. Reduction in tissue impedance during treatment due to charge buildup and membrane rupture can cause increased current flow which engenders additional heating at the treatment site. With reference to FIG. 6, prior treatment methods have suffered from a need to cease treatment when the current exceeds a maximum allowable such that treatment goals are not met. As with direct temperature monitoring, the present invention can avoid the need to stop treatment by reducing the applied voltage and thus current through the tissue to control and prevent undesirable clinically significant thermal effects. Modulation of pulse duration and pulse burst interval duration may also be employed by the controller 11 for this purpose as described.

Figures 11, 12:
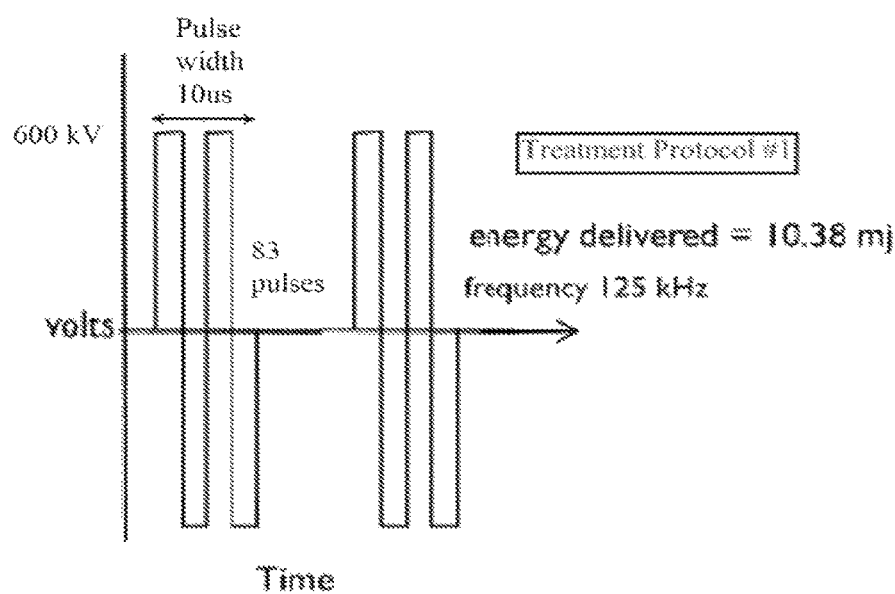
FIG. 11 is a chart of exemplary treatment protocol parameters according to the present invention.
FIG. 12 is a diagram of the parameters of exemplary treatment protocol number 1.

With reference to FIG. 11, four exemplary RF-EMB treatment protocols are detailed. With additional reference to FIG. 12, in protocol 1, a pulse train of 83 pulses 32 each a 10 ms duration is applied at 600 volts to electrodes spaced at 1 cm resulting in a field strength of 600 V/cm between the electrodes. In this example the applied pulses are bipolar with a frequency of 125 kHz with a pulse width of 10 ms, such that the total energy applied over the 0.83 seconds duration of the pulse train was 10.38 mJ. These treatment models and the total energy delivered were referenced from work describing energy parameters used for membrane breakdown of algae by, Foltz, G., *Algae Lysis With Pulsed Electric Fields*, California State Polytechnic University, San Luis Obispo 2012, downloaded from http://digitalcommons.-calpoly.edu/theses/732/. Foltz demonstrated this energy requirement using unipolar pulses, without the advantage of instant charge reversal pulses, making this the worst case scenario for energy requirements to produce EMB.

Figure 13:
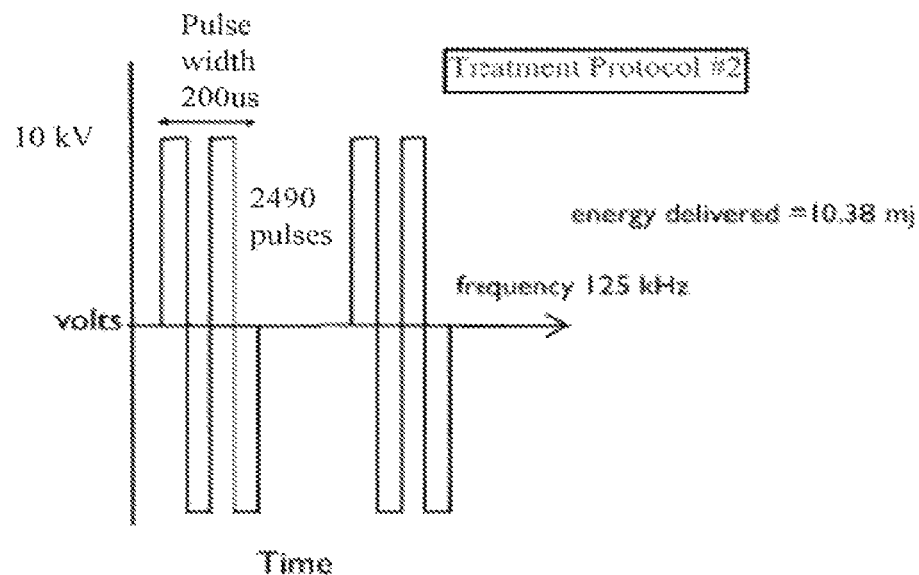
FIG. 13 is a diagram of the parameters of exemplary treatment protocol number 2.
Figure 14:
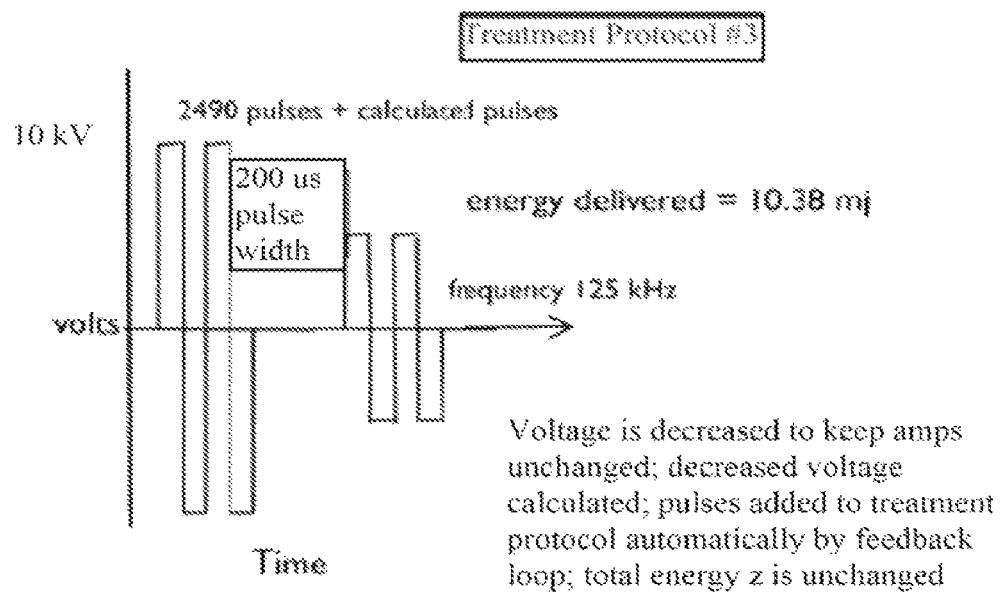
FIG. 14 is a diagram of the parameters of exemplary treatment protocol number 3.
Figure 15:
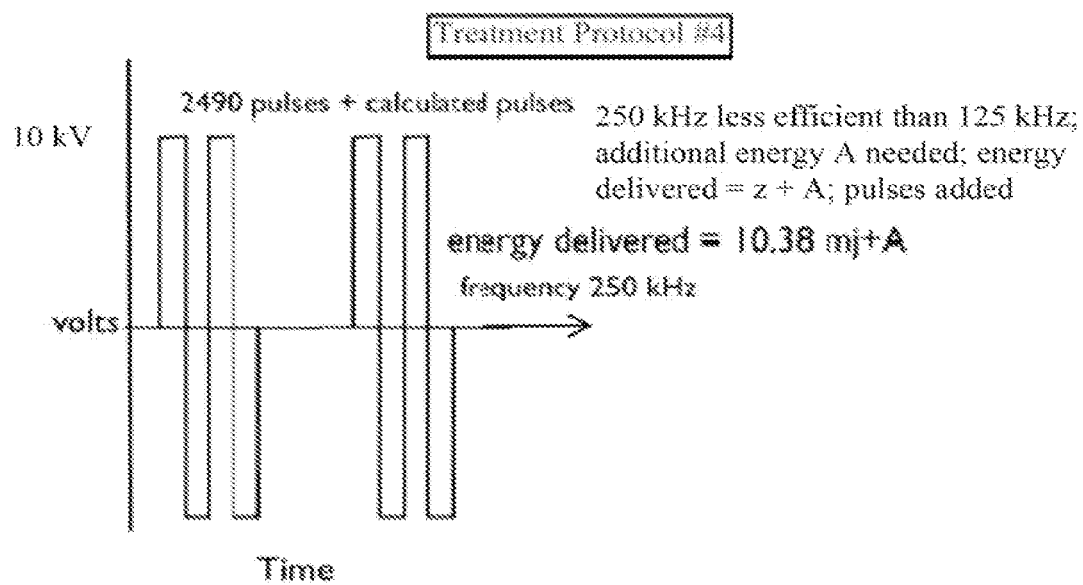
FIG. 15 is a diagram of the parameters of exemplary treatment protocol number 4.

With reference to FIG. 13, in protocol 2 EMB is achieved by a pulse width decreased to 200 µs and pulse train extended to 2490 pulses in a 10 kV/cm field for a total treatment time of 0.49 seconds. The total applied energy is again 10.38 mJ. With reference to FIG. 14, in protocol 3 additional pulses above the initially targeted 2490 are added by the controller 11 to compensate for reduction in voltage/field strength during treatment based on feedback from the treatment site. With reference to FIG. 15, in protocol 4 the additional pulses above the initially targeted 2490 are added to compensate for loss of efficiency resulting from the 250 kHz signal as compared to the 125 kHz signal frequency in the previous exemplary protocols.

The method of ablating undesirable soft tissue of the present invention is carried out by first identifying the location of the soft tissue within the subject to be ablated. Tissue identification may be done by known medical imaging techniques such as ultrasound, CT or MRI. The target soft tissue may or may not be a malignancy but rather need only be tissue that is undesirable in its present location for some reason. After identification of the target tissue, the preferred position and spacing of the electrodes relative to target soft tissue is determined based on the location and shape of the tissue to be ablated, the shape and location of adjacent structures, the dielectric constant and the conductivity of the target and surrounding soft tissue. Typically from 1 to 6 needle type probe electrodes are used. The electrodes are introduced into position in and around the treatment and connected to a controller for controlled delivery of the electric pulses for field generation and treatment. The probe electrodes may include a temperature sensor such as a thermocouple for reading and signaling to the controller the local temperature at or near the electrode. Placement and positioning of the electrodes may preferably be confirmed by medical imaging. The pulse generator is activated by the controller to apply electrical pulses to the electrodes to generate the treatment field as described above thereby causing electrical membrane breakdown of some or all of cells of said soft tissue.

Electrical membrane breakdown, unlike IRE or thermal ablation techniques, causes immediate spillage of all intracellular components of the ruptured cells into an extracellular space and exposes the internal constituent part of the cell membrane to the extracellular space. The intracellular components include cellular antigens and the internal constituent parts of the cell membrane include antigens specific to the cell membrane which induce an immunologic response to destroy and remove this and like material in the body of the subject. Like material may be other material in the body of the subject having the same cellular antigens or cell membrane specific antigens at locations remote from the treatment site including metastatic tissue. However, the human body also has natural defense systems for tumors which prevent destruction and/or removal of the tumor in some cases. One of these operates via an inhibitory signal, which presents itself to the body's cytotoxic T lymphocytes (CTLs), the cells in the body that recognize and destroy cancer cells, and binds to the cytototoxic T lymphocyte-associated antigen 4 (CTLA-4) receptor, turning off the cytotoxic reaction that may otherwise destroy the cancer cell.

Thus, according to another embodiment of the present invention, the immunologic response of RF-EMB is enhanced by administration of drugs that increase the immunologic response process including drugs which block inhibition of the CTLA-4 inhibitory signal of cytotoxic lymphocytes, or that bind to the S100-A9 protein, which is involved in modulating regulatory myeloid cell functions. An example of the former drug type is Ipilimumab (marketed as Yervoy®). An example of the latter is Tasquinimod. Such drugs can be administered by any means, including without limitation, intravenously, orally or intramuscularly and may further be injected directly into or adjacent to the target soft tissue immediately before or after applying the EMB electric field or a set number of days before or after an RF-EMB treatment, as described in the sample treatment protocols below. Such immunologic response enhancing drug may be comprised also of autologous dendritic cells. For example, Sipuleucel-T (marketed as Provenge®) therapy uses autologous patient dendritic cells activated with prostatic acid phosphatase (PAP) and infused back into the patient's system. Another relevant immunologic drug is pembrolizumab, which works by blocking a protein known as Programmed Death receptor (PD-1), or a related protein known as PD-L 1, both of which are used by tumors as a defense to tumor-fighting cells. Yet another relevant immunologic drug is cyclophosphamide, which depresses regulatory T cells and interfere with DNA replication. Many immunologic drugs such as those described herein are effective against one or a small handful of cancer types, but are not effective, in isolation, against all cancer types for which this class of drugs was designed to be used.

Combining RF-EMB treatment with the administration of an immunologic drug such as those described above leaves the target cells' antigens intact and exposed to the external environment, allowing them to react with the patient's immune system, all of which aids the functioning of the immunologic drug. The combination treatment may aid in the treatment of patients with one of two distinct disease pathologies. In a first embodiment, comprising a method for treating a patient with a primary cancerous tumor and a high likelihood of micrometastatic disease, RF-EMB may be applied to cause direct destruction of the primary tumor preceded or followed by the administration of a immunologic drug regimen designed to interact cooperatively with the intact antigens which have been exposed as a result of the RF-EMB treatment. The immunologic drug chosen may be one that blocks the inhibitory response that may otherwise prevent the patient's body from recognizing and destroying the RF-EMB target cells and others having the same cellular antigens (i.e., micrometastatic growths) as a result of the RF-EMB treatment. In a second embodiment, comprising a method for treating a patient having advanced metastatic disease, RF-EMB treatment may be administered at midpoints of an ongoing treatment plan utilizing an immunologic drug as described above. Under this embodiment. RF-EMB treatments enhance the effectiveness of the immunologic drug by exposing unique cellular antigens to the patient's immune system.

Three sample treatment protocols for the use of RF-EMB in conjunction with the administration of an immunologic drug are now described. In Example 1, 300 mg/m$^2$ of cyclophosphamide are administered intravenously to the patient on Day 1 of treatment. On Day 3, the patient receives RF-EMB treatment according to one of the four protocols described above with reference to FIG. 11. Beginning two weeks after the RF-EMB treatment and lasting until week 26 following RF-EMB treatment, 25 mg of cyclophosphamide is administered to the patient orally for six cycles, each cycle comprising four weeks, wherein the patient receives an oral dose of cyclophosphamide twice daily in cycles of seven days on (wherein the drug is administered), seven days off (wherein no drug is administered). In Example 2, the patient is treated on Day 1 with RF-EMB treatment according to one of the four protocols described above with reference to FIG. 11. Also on Day 1, the patient is given 3 mg/kg of ipilimumab intravenously over the course of 90 minutes. The patient then receives an additional three doses of ipilimumab, 3 mg/kg intravenously, each dose separated by a period of three weeks. In Example 3, 300 mg/m$^2$ of cyclophosphamide are administered intravenously to the patient on Day 1 of treatment. On Day 3 of treatment, the patient receives RF-EMB treatment according to one of the four protocols described above with reference to FIG. 11, with the addition of the injection of autologous dendritic cells directly into the target rumor. Beginning two weeks after the RF-EMB treatment and lasting until week 26 following RF-EMB treatment, 25 mg of cyclophosphamide is administered to the patient orally for six cycles, each cycle comprising four weeks, wherein the patient receives an oral dose of cyclophosphamide twice daily in cycles of seven days on (wherein the drug is administered), seven days off (wherein no drug is administered).

Electrical membrane breakdown causes immediate, visually observable tissue change, cellular membrane destruction and cell death. As a result, the method may include the biopsy of a portion of the treated target tissue to verify treatment efficacy immediately after completion of the treatment while the patient is still in position for additional treatment. Additional treatment may be immediately administered based on the biopsy result and visual determination of treatment efficacy.

Alternatively, because the intracellular environment comprises a unique chemical composition, such as high potassium and uric acid concentrations, spillage of the cell contents can now be detected by methods such as placing one or more needle probes into critical locations of the treatment area to measure chemical levels using chemical reagents, electrical impedance or resistance measurements, pH measurements, spectroscopy, or the like. Moreover, a device such as a microneedle sensor, comprising one or more sensors capable of measuring the above qualities integrated into or inserted through the hollow core of a microneedle, may be inserted at one or more predetermined locations in the treatment area during an RF-EMB procedure to measure cellular spillage via extracellular chemical composition in real time.

According to this method, in a preferred embodiment, a hollow needle having at least one dimension of less than 1 millimeter (known as a microneedle) is outfitted with one or more sensors by inserting the sensor(s) through the hollow center of the needle. The sensor(s) may be one or more of the types described above, including but not limited to a pH sensor, a lactate sensor, a glucose sensor, an electrical impedance sensor, a potassium sensor, and/or a uric acid sensor. Multiple such sensors may be bundled together or a single sensor could be used which measures one or more of the relevant properties. In an alternative embodiment, the sensor may be a spectrometer. Most preferably, one or more sensor-containing microneedles are inserted into the selected treatment area immediately prior to the application of RF-EMB treatment, and remain inserted into the treated tissue for the entire duration of the treatment session. Readings from the sensors may be measured by any means known in the art. Such a method has the added benefit of allowing the treatment provider to observe and quantify the level of target cell destruction, and thereby treatment efficacy, in real time and in vivo. By contrast, prior art, thermal ablation methods or non thermal ablation methods such as IRE lack this capability in that they do not cause a measurable amount of the cellular contents to be spilled into the extracellular area immediately, resulting instead in thermal necrosis or targeted apoptotic cell death which destroys the cell and its contents before any of the cellular contents are exposed for measurement. Thus, prior art ablation methods often required a biopsy of the treated area to determine treatment efficacy, which cannot be completed until the termination of the treatment.

According to this preferred embodiment, treatment parameters and/or location(s) may be monitored and/or adjusted in real time based on the real time measured levels of cellular spillage during the treatment process. In addition, or alternatively, measurements of the cellular contents as described herein may be taken before, after, or between phases of treatment without the need to subject the patient to a biopsy or other invasive procedure to measure treatment efficacy. Measurement techniques for cellular contents are not limited to those described herein, but may be carried out by any means known in the art of measuring chemical compositions of a targeted treatment area in vivo and/or in real time.

In yet another alternate embodiment of the present invention, with or without intermediate biopsy and visual observation for efficacy, the mode of treatment according to the present invention may be switched from EMB to thermal ablation without removal or repositioning of the electrodes. A switch to thermal ablation may be desirable to control bleeding at the tissue site or for direct destruction of undesirable tissue in concert with the RF-EMB. The switch may occur within a single pulse train by operation of the controller, or may be accomplished by a second or additional pulse train directed to RF thermal ablation only. The switch is accomplished by reconfiguring the signal generated by the pulse generator to increase the tissue temperature at the electrodes according to known RF thermal techniques.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

INDUSTRIAL APPLICABILITY

Studies estimate that cancer kills approximately 20,000 people worldwide per day. Many casualties could be avoided and the quality of life could be improved for many patients with more effective, minimally invasive methods treatment of cancerous tumors and other conditions resulting in unwanted soft tissue. Minimally invasive treatments capable of assisting a patient's own immune system in attacking and removing unwanted or cancerous tissue within the patient's body would further aid in saving lives and improving patient quality of life. What is needed is a minimally invasive method of removal of unwanted soft tissue, such as cancerous tumors. The present invention is an innovative method of ablating unwanted soft tissue within a patient's body that has applicability to many types of cancerous as well as non-cancerous tissue, that significantly improves effectiveness of performing such a procedure, and that further provides a means to directly measure the efficacy of such procedures in vivo and simultaneous with treatment.

The invention claimed is:

1. A system for treating soft tissue in a living subject, the system comprising:
an electric pulse generator;
a probe comprising an electrode electrically connected to the electric pulse generator;
wherein the probe and electric pulse generator are configured to apply to the soft tissue an electric field in a range of 1,500 V/cm to 10,000 V/cm by delivering, from the pulse generator to the probe, a series of bi-polar electric pulses, wherein the electric field is sufficient to cause electrical membrane breakdown of a cell membrane of cells of the soft tissue, including immediate destruction of the cell membrane and spillage of intracellular components into an extracellular space,
wherein the bi-polar electric pulse is characterized by an instant charge reversal between positive and negative polarity.

2. The system of claim 1 wherein a voltage of the bi-polar electric pulses is from 0.5 kV to 10 kV.

3. The system of claim 1, wherein the pulse generator is configured to deliver the series of bi-polar electric pulses such that the voltage over time of the series of bi-polar electric pulses traces a square waveform.

4. The system of claim 1, wherein the pulse generator is configured to deliver the series of bi-polar electric pulses including at least 100 bi-polar electric pulses to the probe.

5. The system of claim 1, wherein the pulse generator is configured to deliver the series of bi-polar electric pulses to the probe, each pulse having a duration of between 100 μs and 1000 μs.

6. The system of claim 1, wherein the probe and electric pulse generator are configured to apply an electric field having a frequency from 14.2 kHz to 500 kHz.

7. The system of claim 6, wherein the probe and electric pulse generator are configured to apply an electric field having frequency from 100 kHz to 450 kHz.

8. The system of claim 1, comprising a controller coupled to the electric pulse generator and configured to control delivery of the series of bi-polar electric pulses.

9. The system of claim 8, wherein the controller is configured to control one or more of a duration of each of the bi-polar electric pulses, a shape of each of the bi-polar electric pulses, a number of the bi-polar electric pulses in the series, and a spacing between successive bi-polar electric pulses in the series.

10. The system of claim 8, comprising a temperature probe connected to the controller,
wherein the controller is configured to control a characteristic of the bi-polar electric pulse responsive to a temperature reading from the temperature probe.

11. The system of claim 10, wherein the temperature probe is integral to the at least one electrode.

12. The system of claim 10, wherein the controller is configured to alter for one or more of a duration of the bi-polar electric pulses in the series, an interval between bi-polar electric pulses in the series, and a total number of bi-polar electric pulses in the series when to the temperature reading does not satisfy a set point.

13. The system of claim 8, wherein the controller is configured to reduce a voltage of the bi-polar electric pulses when a current through the electrode satisfies a threshold.

14. The system of claim 1 wherein the system is configured to enable administration to the subject of an immunologic response enhancing drug.

15. The system of claim 14, wherein system is configured to enable injection of the immunologic response enhancing drug directly into or adjacent to the soft tissue before or after applying the electric field to the soft tissue.

16. The system of claim 14 wherein administration of the immunologic response drug is configured to increase an immunologic process of the subject.

17. The system of claim 14 wherein the system is configured to enable the immunologic response enhancing drug to be administered by one of intravenously, orally and intramuscularly.

18. The system of claim 14 wherein the immunologic response enhancing drug is configured to block inhibition of the CTLA-4 inhibitory signal of cytotoxic lymphocytes.

19. The system of claim 14 wherein the immunologic response enhancing drug comprises autologous dendritic cells.

20. The system of claim 14 wherein the immunologic response enhancing drug is configured to bind to S100-A9 proteins.

21. The system of claim 14 wherein the immunologic response enhancing drug is configured to block a protein selected from a group comprising PD-1 and PD-L1.

22. The system of claim 1, comprising a sensor, the sensor comprising one or more of a pH sensor, a lactate sensor, a glucose sensor, an electrical impedance sensor, a potassium sensor, a uric acid sensor, and a spectrometer.

23. The system of claim 22, wherein the system is configured to determine, based a measurement from the sensor, a treatment efficacy of the treatment of the soft tissue.

24. A system for treating soft tissue in a living subject, the system comprising:
   an electrode;
   a controller comprising an electric pulse generator, wherein the electrode is electrically connected to the controller, and wherein the controller is configured to determine an electric field strength based on a tissue type of the soft tissue and a target position of the electrode;
   determine, based on the determined electric field strength, a bi-polar electric pulse train profile characterized by a number of pulses, and a duration of each pulse, and a voltage of the pulses, wherein the voltage of each pulse is characterized by an instantaneous reversal of polarity; and
   deliver from the pulse generator to the electrode a series of electric pulses according to the electric pulse train profile whereby a pulsed electric field is generated, wherein the electric field is in a range of 1,500 V/cm to 10,000 V/cm, and wherein the electric field is sufficient to cause cell death of cells of the soft tissue by electrical membrane breakdown, including immediate destruction of the cell membrane and spillage of intracellular components into an extracellular space.

25. The system of claim 24, in which the controller is configured to deliver from the pulse generator to the electrode electric pulses having a voltage from 0.5 kV to 10 kV.

26. The system of claim 24, in which the controller is configured to deliver electric pulses to the probe, each pulse having a duration of between 100 μs and 1000 μs.

27. The system of claim 24, in which the controller is configured to deliver electric pulses to the electrode such that the pulsed electric field has a frequency from 14.2 kHz to 500 kHz.

28. The system of claim 24, in which the system is configured to enable administration to the subject of an immunologic response enhancing drug.

29. The system of claim 28, wherein the system is configured to enable the immunologic response enhancing drug to be injected directly into or adjacent to the soft tissue before or after applying the electric field to the soft tissue.

30. The system of claim 24, in which the controller is configured to determine a minimum energy profile based on the tissue type of the soft tissue, and to determine the electric field strength based on the determined minimum energy profile.

* * * * *